US011530266B2

(12) United States Patent
Gyobu et al.

(10) Patent No.: US 11,530,266 B2
(45) Date of Patent: Dec. 20, 2022

(54) ANTI-PODOPLANIN ANTIBODY

(71) Applicants: JAPANESE FOUNDATION FOR CANCER RESEARCH, Tokyo (JP); API CO., LTD., Gifu (JP)

(72) Inventors: Nobuhiko Gyobu, Gifu (JP); Naoya Fujita, Tokyo (JP); Mamoru Kakino, Gifu (JP); Ai Kawashima, Tokyo (JP); Shinya Fujihara, Gifu (JP); Naoki Goda, Gifu (JP)

(73) Assignee: JAPANESE FOUNDATION FOR CANCER RESEARCH, Tokyo (JP)

(*) Notice: Subject to any disclaimer, the term of this patent is extended or adjusted under 35 U.S.C. 154(b) by 0 days.

(21) Appl. No.: 16/626,162

(22) PCT Filed: Jun. 14, 2019

(86) PCT No.: PCT/JP2019/023682
§ 371 (c)(1),
(2) Date: Dec. 23, 2019

(87) PCT Pub. No.: WO2020/188836
PCT Pub. Date: Sep. 24, 2020

(65) Prior Publication Data
US 2021/0403555 A1    Dec. 30, 2021

(30) Foreign Application Priority Data

Mar. 15, 2019 (JP) .............................. JP2019-048861

(51) Int. Cl.
*C07K 16/28* (2006.01)
*C07K 16/46* (2006.01)
*A61K 39/00* (2006.01)

(52) U.S. Cl.
CPC ........ *C07K 16/2803* (2013.01); *C07K 16/462* (2013.01); *A61K 2039/505* (2013.01); *C07K 2317/24* (2013.01); *C07K 2317/565* (2013.01); *C07K 2317/567* (2013.01); *C07K 2317/76* (2013.01); *C07K 2317/92* (2013.01)

(58) Field of Classification Search
CPC ............ C07K 2317/565; C07K 16/465; C07K 16/464
USPC ...................................................... 424/133.1
See application file for complete search history.

(56) References Cited

U.S. PATENT DOCUMENTS

| 10,730,939 | B2* | 8/2020 | Fujita ...................... C07K 7/06 |
| 2016/0347834 | A1 | 12/2016 | Kato et al. |
| 2018/0237518 | A1 | 8/2018 | Fujita et al. |
| 2021/0009683 | A1* | 1/2021 | Fujita ...................... C07K 16/30 |

FOREIGN PATENT DOCUMENTS

| WO | WO 2015/053381 A1 | 4/2015 |
| WO | WO 2017/010463 A1 | 1/2017 |

OTHER PUBLICATIONS

Almagro & Franssen, Frontiers in Bioscience 13:1619-33 (2008).*
Edwards et al., Mol Biol 334:103-118 (2003).*
Marchalonis et al., Dev & Comp Immunol. 30:223-247 (2006).*
Lippow et al., "Computational design of antibody-affinity improvement beyond in vivo maturation," Nature Biotechnology, 25(10): 1171-1176 (2007).*
Sulea et al., "Application of Assisted Design of Antibody and Protein Therapeutics (ADAPT) improves efficacy of a Clostridium difficile toxin A single-domain antibody," Scientific Reports, 8(260):1-11 (2018).*
Hasegawa et al., "Single amino acid substitution in LC-CDR1 induces Russell body phenotype that attenuates cellular protein synthesis through eIF2a phosphorylation and thereby downregulates IgG secretion despite operational secretory pathway traffic," MABS, vol. 9, No. 5, pp. 854-873 (2017) (PTO-892).*
Altshuler et al., "Generation of Recombinant Antibodies and Means for Increasing Their Affinity," Biochemistry (Moscow), 75(13): 1584-1605 (2010).*
Vajda et al., "Progress toward improved understanding of antibody maturation," Current Opinion in Structural Biology, 67 pp. 226-231 (2021).*
Marks et al., "How repertoire data are changing antibody science," J. Biol. Chem. 295(29) 9823-9837 (2020).*
Akbar et al., Cell Reports 34, 108856, Mar. 16, 2021.*
Lo et al., BMC Genomics vol. 22, Article No. 116 (2021).*
Ukaji et al. (CancerSci 112(6):2299-2313 (Jun. 2021)).*
Ukaji et al (Oncotarget 9(70): 33322-33336 (Sep. 7, 2018; Published online Sep. 7, 2018).*
Sekiguchi et al. (Cancer Research, (2016) vol. 76, No. 14, Supp. Supplement. Abstract No. 1275; Meeting Info: 107th Annual Meeting of the American Association for Cancer Research, AACR 2016. New Orleans, LA, United States. Apr. 16, 2016-Apr. 20, 2016).*
Arszumi et al., "Expression of podoplanin in human bone and bone tumors: New marker of osteogenic and chondrogenic bone tumors", Pathology International, 2010; vol. 60, pp. 193-202.
Fujita, "Development of therapeutic antibodies targeting Aggrus /podoplanin", Journal of Clinical and Experimental Medicine (Igaku No Ayumi), 2018, vol. 265, No. 1, pp. 60-65.
Fukunaga, "Expression of D2-40 in lymphatic endothelium of normal tissues and in vascular tumours", Histopathology 2005, vol. 46, pp. 396-402.
Huse et al., "D2-40 functions as an effective chondroid marker distinguishing true chondroid tumors from chordoma", Acta Neuropathol, 2007, vol. 113, pp. 87-94.

(Continued)

*Primary Examiner* — Lynn A Bristol
(74) *Attorney, Agent, or Firm* — Birch, Stewart, Kolasch & Birch, LLP

(57) ABSTRACT

The object of the present invention is to provide a humanized or mouse-human chimeric anti-podoplanin antibody or an antibody fragment containing the antigen-binding region thereof, and the object is achieved by providing an isolated humanized or mouse-human chimeric anti-podoplanin antibody which comprises a predetermined amino acid sequence, or an antibody fragment containing the antigen-binding region thereof.

12 Claims, 5 Drawing Sheets
Specification includes a Sequence Listing.

(56) References Cited

OTHER PUBLICATIONS

International Search Report (PCT/ISA/210) issued in PCT/JP2019/023682, dated Sep. 3, 2019.

Kaneko et al., "Anti-podoplanin Monoclonal Antibody LpMab-7 Detects Metastatic Lesions of Osteosarcoma", Monoclonal Antibodies In Immunodiagnosis and Immunotherapy, 2015, vol. 34, No. 3, pp. 154-161.

Kato et al., "Enhanced Expression of Aggrus (T1alpha/Podoplanin), a Platelet-Aggregation-Inducing Factor in Lung Squamous Cell Carcinoma", Tumor Biology, 2005, vol. 26, pp. 195-200.

Kunita et al., "Podoplanin Is Regulated by AP-1 and Promotes Platelet Aggregation and Cell Migration in Osteosarcoma", The American journal of Pathology, 2011, vol. 179, No. 2, pp. 1041-1049.

Mishima et al., "Increased expression of podoplanin in malignant astrocytic tumors as a novel molecular marker of malignant progression", Acta Neuropalhol, 2006, vol. 111, pp. 483-488.

Oki et al., "Development of high-sensitive anti-podoplanin mAbs against osteosarcoma", Japan Journal of Molecular Tumor Marker Research, 2015, vol. 30, pp. 70-71.

Ordonez, "D2-40 and podoplanin are highly specific and sensitive immunohistochemical markers of epithelioid malignant mesothelioma", Human Pathology, 2005, vol. 36, pp. 372-380.

Schacht et al., "Up-Regulation of the Lymphatic Marker Podoplanin, a Mucin-Type Transmembrane Glycoprotein, in Human Squamous Cell Carcinomas and Germ Cell Tumors", American journal of Pathology, 2005, vol. 166, No. 3, pp. 913-921.

Sekiguchi et al., "Targeting a novel domain in podoplanin for inhibiting plateletmediated tumor metastasis", Oncotarget, 2015, vol. 7, No. 4, pp. 3934-3946.

Suzuki-Inoue, "Cancer progression and platelets", Japanese Journal of Thrombosis and Hemostasis, 2016, vol. 27, No. 1, pp. 3-10.

Suzuki-Inoue, "CLEC-2/podoplanin and thromboinflammation", Blood, 2017, vol. 129, No. 14, pp. 1896-1898.

Suzuki-Inoue, "Identification of the platelet activation receptor CLEC-2, its endogenous ligand podoplanin, and pathophysioloaical roles of their interaction", Japanese Journal of Thrombosis and Hemostasis, 2017, vol. 28, No. 4, pp. 518-526.

Takagi et al., "Expression of Aggrus/podoplanin in bladder cancer and its role in pulmonary metastasis", International Journal of Cancer, 2014, vol. 134, pp. 2605-2614.

Takemoto et al., "Platelet-activating factor podoplanin: from discovery to drug development", Cancer Metastasis Rev 2017, vol. 36, pp. 225-234.

Takemoto et al., "The novel target for developing cancer metastasis therapy: the cancer-platelet interaction", Japanese Journal of Thrombosis and Hemostasis, 2016, vol. 7, No. 1, pp. 11-17.

Wicki et al., "Tumor invasion in the absence of epithelial-mesenchymal transition: Podoplanin-mediated remodeling of the actin cytoskeleton", Cancer Cell, 2006, vol. 9, pp. 261-272.

Written Opinion (PCT/ISA/237) issued in PCT/JP2019/023682, dated Sep. 3, 2019.

Xu et al., "High-level expression of podoplanin in benign and malignant soft tissue tumors: immunohistochemical and quantitative real-time RT-PCR analysis", Oncology Reports, 2011, vol. 25, pp. 599-607.

Safdari et al., "Antibody humanization methods—a review and update," Biotechnology and Genetic Engineering Reviews (2013), vol. 29, No. 2, pp. 175-186.

\* cited by examiner

ANTI-PODOPLANIN ANTIBODY

TECHNICAL FIELD

The present invention relates to an anti-podoplanin antibody, particularly a humanized or mouse-human chimeric anti-podoplanin antibody or an antibody fragment containing the antigen-binding region thereof.

BACKGROUND ART

It is reported that platelets aggregate and coat the cell membrane of cancer cells to enhance resistance to blood flow-induced shear stress and to promote evasion from immune cell attack, which results in increased survival of metastatic cancer cells, and that platelet aggregation facilitates tumor mass formation and embolization, and, moreover, promotes formation of metastatic lesions by mechanisms involving, for example, promotion of tumor proliferation, epithelial-mesenchymal transition (EMT), and angiogenesis (Non-Patent Documents 1 and 2).

Meanwhile, podoplanin has been identified on cancer cells as a protein that induces platelet aggregation, and is reported to bind to CLEC-2, a receptor on platelets, through its PLAG domains, preferably PLAG4 domain (Non-Patent Documents 1 to 4).

Podoplanin is also reported to be highly expressed in cancers, such as mesothelioma, brain tumor, testis tumor, Kaposi's sarcoma, lymphangioma, cavernous hemangioma, angiosarcoma, lung squamous cell carcinoma, ovarian dysgerminoma, glioma, germ cell tumor, head and neck cancer, lung cancer, bladder cancer, bone and soft tissue sarcoma (primary bone tumor (osteosarcoma, chondrosarcoma), soft tissue sarcoma), and esophagus cancer, and to enhance the invasive and metastatic capabilities of cancer cells (Non-Patent Documents 5 to 17).

Accordingly, it has been suggested that inhibition of the binding between podoplanin on cancer cells and CLEC-2 on platelets results in reduced tumor mass formation and embolization, and, moreover, suppressed formation of metastatic lesions due to reduced tumor proliferation, epithelial-mesenchymal transition (EMT), and angiogenesis, which can lead to prevention of cancer-associated thrombosis (Non-Patent Documents 1 and 4). Since it is reported that podoplanin expression is elevated in the vein wall during venous thrombosis and thrombosis causes inflammation, prevention of thrombosis can be expected to prevent inflammation (Non-Patent Documents 4 and 18) and, moreover, to suppress infiltration and metastasis of the above-described cancers.

Under such conditions, novel therapeutic agents that inhibit the binding between podoplanin on cancer cells and CLEC-2 on platelets are being developed. As one of the therapeutic agents, the antibody PG4D2 (of IgG2a subclass), which is an anti-human podoplanin antibody targeted for the PLAG4 domain, has been established (Non-Patent Document 1, Patent Document 1). It has also been observed that the antibody has very high avidity, as indicated by an equilibrium dissociation constant ($K_D$) of 0.3 nM or less, and also has an activity to reduce frequencies of podoplanin-positive, tumor cell-dependent, platelet aggregation and metastasis.

However, the antibody PG4D2 is a mouse antibody obtained from an immunized mouse, and neither humanized antibody nor mouse-human chimeric antibody against podoplanin has been established. Any mouse antibody has a relatively short in vivo half-life in human bodies. Moreover, any mouse antibody is highly immunogenic in human subjects and thus has a limited therapeutic value for human subjects. It is concerned that long-term or repeated administration of the mouse antibody causes an immune response, which may increase the risk of adverse allergic reaction in patients. Hence, there is a need for a humanized or mouse-human chimeric antibody in the technical field of interest.

PRIOR ART DOCUMENT

Patent Document

Patent Document 1: WO2017/010463

Non-Patent Document

Non-Patent Document 1: J. Clin. Exp. Med. (Igaku No Ayumi), 265(1), 60-65 (2018)
Non-Patent Document 2: Jpn. J. Thromb. Hemost., 27(1), 3-10 (2016)
Non-Patent Document 3: Jpn. J. Thromb. Hemost., 27(1), 11-17 (2016)
Non-Patent Document 4: Jpn. J. Thromb. Hemost., 28(4), 518-526 (2017)
Non-Patent Document 5: "#30. Development of high-sensitive anti-podoplanin mAbs against osteosarcoma," Internet www.jstage.jst.go.jp/article/jsmtmr/30/0/30_70/_pdf>, [Accessed: Jan. 21, 2019]
Non-Patent Document 6: Histopathology, April; 46(4):396-402 (2005)
Non-Patent Document 7: Hum. Pathol., April; 36(4):372-80 (2005)
Non-Patent Document 8: Tumour Biol., July-August; 26(4): 195-200 (2005)
Non-Patent Document 9: Am. J. Pathol., March; 166(3):913- (2005)
Non-Patent Document 10: Acta Neuropathol., May; 111 (5):483-8 (2006)
Non-Patent Document 11: Cancer Cell, April; 9(4):261-72 (2006)
Non-Patent Document 12: Acta Neuropathol., January; 113 (1):87-94 (2007)
Non-Patent Document 13: Int. J. Cancer, June 1; 134(11): 2605-14 (2014)
Non-Patent Document 14: Pathol. Int., March; 60(3):193-202 (2010)
Non-Patent Document 15: Oncol. Rep., March; 25(3):599-607 (2011)
Non-Patent Document 16: Am. J. Pathol., August; 179(2): 1041-9 (2011)
Non-Patent Document 17: Monoclon. Antib. Immunodiagn. Immunother., June; 34(3):154-61 (2015)
Non-Patent Document 18: Blood, April 6; 129(14):1896-1898 (2017)

SUMMARY OF INVENTION

Problems to be Solved by the Invention

The object of the present invention is to provide a humanized or mouse-human chimeric anti-podoplanin antibody or an antibody fragment containing the antigen-binding region thereof.

Means for Solving the Problem

The present inventors studied hard and consequently found that the above-described object is achieved by using predetermined sequences for humanization or mouse-human chimerization of the mouse antibody PG4D2, and completed the present invention.

The present invention is as follows.

The present invention is an isolated humanized or mouse-human chimeric anti-podoplanin antibody which comprises the following amino acid sequences, or an antibody fragment containing the antigen-binding region thereof, provided that the amino acid sequences of the heavy-chain CDRs 1 to 3 and the light-chain CDRs 1 to 3 optionally have a sequence identity of not less than 90% to the amino acid sequences represented by SEQ ID NOs: 1 to 6 below, respectively;

wherein the amino acid sequence of the heavy-chain CDR1 is the amino acid sequence represented by SEQ ID NO: 1, the amino acid sequence of the heavy-chain CDR2 is the amino acid sequence represented by SEQ ID NO: 2, the amino acid sequence of the heavy-chain CDR3 is the amino acid sequence represented by SEQ ID NO: 3, the amino acid sequence of the light-chain CDR1 is the amino acid sequence represented by SEQ ID NO: 4, the amino acid sequence of the light-chain CDR2 is the amino acid sequence represented by SEQ ID NO: 5, and the amino acid sequence of the light-chain CDR3 is the amino acid sequence represented by SEQ ID NO: 6.

In a preferred aspect of the anti-podoplanin antibody or antibody fragment containing the antigen-binding region thereof, the anti-podoplanin antibody is a humanized antibody which comprises a variable region comprising the amino acid sequence I or II below, provided that the amino acid sequences of the heavy-chain FRs 1 to 4 and the light-chain FRs 1 to 4 in the following amino acid sequence I optionally have a sequence identity of not less than 90% to the amino acid sequences represented by SEQ ID NOs: 7 to 14 below, respectively, and the amino acid sequences of the heavy-chain FRs 1 to 4 and the light-chain FRs 1 to 4 in the following amino acid sequence II optionally have a sequence identity of not less than 90% to the amino acid sequences represented by SEQ ID NOs: 7, 15, 16, 10 to 14 below, respectively;

wherein, in the amino acid sequence I, the amino acid sequence of the heavy-chain CDR1 is the amino acid sequence represented by SEQ ID NO: 1, the amino acid sequence of the heavy-chain CDR2 is the amino acid sequence represented by SEQ ID NO: 2, the amino acid sequence of the heavy-chain CDR3 is the amino acid sequence represented by SEQ ID NO: 3, the amino acid sequence of the light-chain CDR1 is the amino acid sequence represented by SEQ ID NO: 4, the amino acid sequence of the light-chain CDR2 is the amino acid sequence represented by SEQ ID NO: 5, the amino acid sequence of the light-chain CDR3 is the amino acid sequence represented by SEQ ID NO: 6, the amino acid sequence of the heavy-chain FR1 is the amino acid sequence represented by SEQ ID NO: 7, the amino acid sequence of the heavy-chain FR2 is the amino acid sequence represented by SEQ ID NO: 8, the amino acid sequence of the heavy-chain FR3 is the amino acid sequence represented by SEQ ID NO: 9, the amino acid sequence of the heavy-chain FR4 is the amino acid sequence represented by SEQ ID NO: 10, the amino acid sequence of the light-chain FR1 is the amino acid sequence represented by SEQ ID NO: 11, the amino acid sequence of the light-chain FR2 is the amino acid sequence represented by SEQ ID NO: 12, the amino acid sequence of the light-chain FR3 is the amino acid sequence represented by SEQ ID NO: 13, and the amino acid sequence of the light-chain FR4 is the amino acid sequence represented by SEQ ID NO: 14; and wherein, in the amino acid sequence II, the amino acid sequence of the heavy-chain CDR1 is the amino acid sequence represented by SEQ ID NO: 1, the amino acid sequence of the heavy-chain CDR2 is the amino acid sequence represented by SEQ ID NO: 2, the amino acid sequence of the heavy-chain CDR3 is the amino acid sequence represented by SEQ ID NO: 3, the amino acid sequence of the light-chain CDR1 is the amino acid sequence represented by SEQ ID NO: 4, the amino acid sequence of the light-chain CDR2 is the amino acid sequence represented by SEQ ID NO: 5, the amino acid sequence of the light-chain CDR3 is the amino acid sequence represented by SEQ ID NO: 6, the amino acid sequence of the heavy-chain FR1 is the amino acid sequence represented by SEQ ID NO: 7, the amino acid sequence of the heavy-chain FR2 is the amino acid sequence represented by SEQ ID NO: 15, the amino acid sequence of the heavy-chain FR3 is the amino acid sequence represented by SEQ ID NO: 16, the amino acid sequence of the heavy-chain FR4 is the amino acid sequence represented by SEQ ID NO: 10, the amino acid sequence of the light-chain FR1 is the amino acid sequence represented by SEQ ID NO: 11, the amino acid sequence of the light-chain FR2 is the amino acid sequence represented by SEQ ID NO: 12, the amino acid sequence of the light-chain FR3 is the amino acid sequence represented by SEQ ID NO: 13, and the amino acid sequence of the light-chain FR4 is the amino acid sequence represented by SEQ ID NO: 14.

In a preferred aspect of the anti-podoplanin antibody or antibody fragment containing the antigen-binding region thereof, the anti-podoplanin antibody is a mouse-human chimeric antibody which comprises variable regions comprising the following amino acid sequences, provided that the amino acid sequences of the heavy-chain FRs 1 to 4 and the light-chain FRs 1 to 4 optionally have a sequence identity of not less than 90% to the amino acid sequences represented by SEQ ID NO: 17 to 24 below, respectively, wherein the amino acid sequence of the heavy-chain CDR1 is the amino acid sequence represented by SEQ ID NO: 1, the amino acid sequence of the heavy-chain CDR2 is the amino acid sequence represented by SEQ ID NO: 2, the amino acid sequence of the heavy-chain CDR3 is the amino acid sequence represented by SEQ ID NO: 3, the amino acid sequence of the light-chain CDR1 is the amino acid sequence represented by SEQ ID NO: 4, the amino acid sequence of the light-chain CDR2 is the amino acid sequence represented by SEQ ID NO: 5, the amino acid sequence of the light-chain CDR3 is the amino acid sequence represented by SEQ ID NO: 6, the amino acid sequence of the heavy-chain FR1 is the amino acid sequence represented by SEQ ID NO: 17, the amino acid sequence of the heavy-chain FR2 is the amino acid sequence represented by SEQ ID NO: 18, the amino acid sequence of the heavy-chain FR3 is the amino acid sequence represented by SEQ ID NO: 19, the amino acid sequence of the heavy-chain FR4 is the amino acid sequence represented by SEQ ID NO: 20, the amino acid sequence of the light-chain FR1 is the amino acid sequence represented by SEQ ID NO: 21, the amino acid sequence of the light-chain FR2 is the amino acid sequence represented by SEQ ID NO: 22, the amino acid sequence of the light-chain FR3 is the amino acid sequence represented by SEQ ID NO: 23, and the amino acid sequence of the light-chain FR4 is the amino acid sequence represented by SEQ ID NO: 24.

In a preferred aspect of the anti-podoplanin antibody or antibody fragment containing the antigen-binding region thereof, the anti-podoplanin antibody comprises a constant region of a human antibody of the IgG class.

Additionally, the present invention provides an agent for inhibiting the binding between podoplanin and CLEC-2 which comprises the anti-podoplanin antibody or antibody fragment containing the antigen-binding region thereof.

Additionally, the present invention provides a pharmaceutical composition which comprises the anti-podoplanin antibody or antibody fragment containing the antigen-binding region thereof.

In a preferred aspect, the pharmaceutical composition is for reducing the proliferation or metastasis of a cancer cell.

In a preferred aspect, the pharmaceutical composition is also for inhibiting platelet aggregation, thrombosis, or inflammation.

Also in a preferred aspect of the pharmaceutical composition, the cancer cell is a podoplanin-positive tumor cell.

Additionally, the present invention provides a DNA segment(s) encoding the protein moiety(ies) of the anti-podoplanin antibody or antibody fragment containing the antigen-binding region thereof.

Additionally, the present invention provides a recombinant vector comprising the DNA segment(s).

Additionally, the present invention provides a host cell comprising the DNA segment(s) or the recombinant vector.

Advantageous Effect of Invention

By the present invention, a humanized or mouse-human chimeric anti-podoplanin antibody or an antibody fragment containing the antigen-binding region thereof can be provided. The anti-podoplanin antibody or antibody fragment containing the antigen-binding region thereof acts to inhibit the binding between podoplanin on cancer cells and CLEC-2 on platelets and is therefore useful as, for example, a pharmaceutical composition intended for reducing the proliferation or metastasis of cancer cells and/or for inhibiting platelet aggregation, thrombosis, or inflammation.

DETAILED DESCRIPTION OF INVENTION

Figure 1:
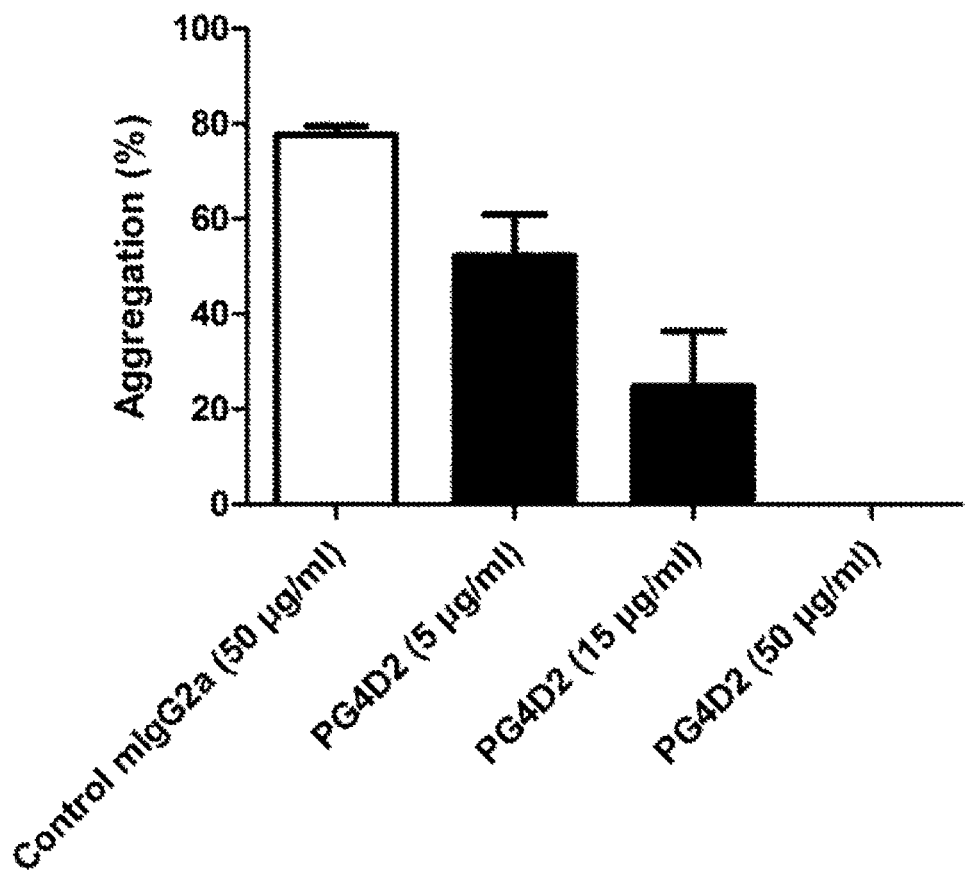
FIG. 1 shows the inhibitory effect of the mouse antibody PG4D2 on in vitro platelet aggregation in an example of the present invention.

Now, the present invention will be described in detail below.

In this specification, the amino acid sequences of the antibodies are in accordance with the Kabat definition.

The present invention is an isolated humanized (including a fully human antibody) or mouse-human chimeric anti-podoplanin antibody which comprises the following amino acid sequences, or an antibody fragment containing the antigen-binding region thereof, wherein the amino acid sequence of the heavy-chain CDR1 is the amino acid sequence represented by SEQ ID NO: 1, the amino acid sequence of the heavy-chain CDR2 is the amino acid sequence represented by SEQ ID NO: 2, the amino acid sequence of the heavy-chain CDR3 is the amino acid sequence represented by SEQ ID NO: 3, the amino acid sequence of the light-chain CDR1 is the amino acid sequence represented by SEQ ID NO: 4, the amino acid sequence of the light-chain CDR2 is the amino acid sequence represented by SEQ ID NO: 5, and the amino acid sequence of the light-chain CDR3 is the amino acid sequence represented by SEQ ID NO: 6.

The amino acid sequences of the heavy-chain CDRs 1 to 3 and the light-chain CDRs 1 to 3 may have a sequence identity of not less than 90%, preferably not less than 95%, to the amino acid sequences represented by SEQ ID NOs: 1 to 6, respectively.

That is, the amino acid sequences of the heavy-chain CDRs 1 to 3 and the light-chain CDRs 1 to 3 may have a sequence identity of not less than 90%, preferably not less than 95%, to the amino acid sequences represented by SEQ ID NOs: 1 to 6, respectively, provided that the antigen-binding activity of an anti-podoplanin antibody comprising those CDRs or an antibody fragment containing the antigen-binding region thereof is substantially the same as that of the above anti-podoplanin antibody or antibody fragment containing the antigen-binding region thereof.

Additionally, the amino acid sequences of the heavy-chain CDRs 1 to 3 and the light-chain CDRs 1 to 3 may have a sequence identity of not less than 90%, preferably not less than 95%, to the amino acid sequences represented by SEQ ID NOs: 1 to 6, respectively, provided that an anti-podoplanin antibody comprising those CDRs or an antibody fragment containing the antigen-binding region thereof has an activity to inhibit the binding of podoplanin to CLEC-2 on platelets.

An amino acid sequence that matches with a predetermined amino acid sequence at a specified identity level refers to an amino acid sequence comprising one or more amino acid substitutions, deletions, insertions, and/or additions that occur at positions in the predetermined amino acid sequence.

The substitution is preferably a conservative substitution. The "conservative substitution" refers to substituting an amino acid residue with another chemically similar amino acid residue in such a manner that the activity of the original peptide is not substantially changed. Examples of the conservative substitution include substituting a hydrophobic residue with another hydrophobic residue, substituting a polar residue with another polar residue of similar charge, and the like. Functionally similar and mutually substitutable amino acids include the following examples. Non-polar (hydrophobic) amino acids include, for example, alanine, valine, isoleucine, leucine, proline, tryptophan, phenylalanine, and methionine; polar (neutral) amino acids include, for example, glycine, serine, threonine, tyrosine, glutamine, asparagine, and cysteine; positively charged (basic) amino acids include, for example, arginine, histidine, and lysine;

additionally, negatively charged (acidic) amino acids include, for example, aspartic acid and glutamic acid.

The term "isolated" in the present invention means that a material is removed from an organism. For example, an antibody that has been produced in an individual and still exists in the individual is not encompassed by the term.

The "humanized antibody" of the present invention comprises variable regions, each comprising complementarity-determining regions derived from the known mouse antibody PG4D2 and framework regions derived from a human antibody, and constant regions derived from a human antibody. The human antibody is not limited by a particular subtype as long as the effects of the present invention are achieved, but the subclass is preferably IgG, more preferably IgG4. The constant regions have, for example, the amino acid sequences of the constant regions of the antibody of the IgG4 subclass, which include the amino acid sequence represented by SEQ ID NO: 25 as the amino acid sequence of the heavy-chain constant region and the amino acid sequence represented by SEQ ID NO: 26 as the amino acid sequence of the light-chain constant region. Additionally, the "humanized antibody" of the present invention may be a "fully human antibody."

The "mouse-human chimeric antibody" of the present invention comprises variable regions derived from the known mouse antibody PG4D2 and constant regions derived from a human antibody. The human antibody is not limited by a particular subtype as long as the effects of the present invention are achieved, but the subclass is preferably IgG, more preferably IgG4. The constant regions have, for example, the amino acid sequences of the constant regions of the antibody of the IgG4 subclass, which include the amino acid sequence represented by SEQ ID NO: 25 as the amino acid sequence of the heavy-chain constant region and the amino acid sequence represented by SEQ ID NO: 26 as the amino acid sequence of the light-chain constant region, as described above.

The phrase "an antibody fragment containing an antigen-binding region" in the present invention refers to a protein containing a portion of the antibody and being capable of binding to the antigen thereof. Examples of such an antibody fragment include a F(ab')2, a Fab', a Fab, a Fv (variable fragment of antibody), a disulfide-linked Fv, single-chain antibody (scFv), and a combination of these polymers. The antibody fragment may be conjugated with a functional molecule(s), such as a non-peptide polymer such as polyethylene glycol (PEG), a radioactive substance, a toxin, a small molecular compound, a cytokine, a growth factor, albumin, an enzyme, and/or another antibody, by chemical or genetic engineering approaches.

The anti-podoplanin antibody or antibody fragment containing the antigen-binding region thereof is preferably a humanized antibody as long as the effects of the present invention are achieved, in which either of the variable regions preferably comprises the amino acid sequence I or II below, wherein, in the amino acid sequence I, the amino acid sequence of the heavy-chain CDR1 is the amino acid sequence represented by SEQ ID NO: 1, the amino acid sequence of the heavy-chain CDR2 is the amino acid sequence represented by SEQ ID NO: 2, the amino acid sequence of the heavy-chain CDR3 is the amino acid sequence represented by SEQ ID NO: 3, the amino acid sequence of the light-chain CDR1 is the amino acid sequence represented by SEQ ID NO: 4, the amino acid sequence of the light-chain CDR2 is the amino acid sequence represented by SEQ ID NO: 5, the amino acid sequence of the light-chain CDR3 is the amino acid sequence represented by SEQ ID NO: 6, the amino acid sequence of the heavy-chain FR1 is the amino acid sequence represented by SEQ ID NO: 7, the amino acid sequence of the heavy-chain FR2 is the amino acid sequence represented by SEQ ID NO: 8, the amino acid sequence of the heavy-chain FR3 is the amino acid sequence represented by SEQ ID NO: 9, the amino acid sequence of the heavy-chain FR4 is the amino acid sequence represented by SEQ ID NO: 10, the amino acid sequence of the light-chain FR1 is the amino acid sequence represented by SEQ ID NO: 11, the amino acid sequence of the light-chain FR2 is the amino acid sequence represented by SEQ ID NO: 12, the amino acid sequence of the light-chain FR3 is the amino acid sequence represented by SEQ ID NO: 13, and the amino acid sequence of the light-chain FR4 is the amino acid sequence represented by SEQ ID NO: 14; and wherein, in the amino acid sequence II, the amino acid sequence of the heavy-chain CDR1 is the amino acid sequence represented by SEQ ID NO: 1, the amino acid sequence of the heavy-chain CDR2 is the amino acid sequence represented by SEQ ID NO: 2, the amino acid sequence of the heavy-chain CDR3 is the amino acid sequence represented by SEQ ID NO: 3, the amino acid sequence of the light-chain CDR1 is the amino acid sequence represented by SEQ ID NO: 4, the amino acid sequence of the light-chain CDR2 is the amino acid sequence represented by SEQ ID NO: 5, the amino acid sequence of the light-chain CDR3 is the amino acid sequence represented by SEQ ID NO: 6, the amino acid sequence of the heavy-chain FR1 is the amino acid sequence represented by SEQ ID NO: 7, the amino acid sequence of the heavy-chain FR2 is the amino acid sequence represented by SEQ ID NO: 15, the amino acid sequence of the heavy-chain FR3 is the amino acid sequence represented by SEQ ID NO: 16, the amino acid sequence of the heavy-chain FR4 is the amino acid sequence represented by SEQ ID NO: 10, the amino acid sequence of the light-chain FR1 is the amino acid sequence represented by SEQ ID NO: 11, the amino acid sequence of the light-chain FR2 is the amino acid sequence represented by SEQ ID NO: 12, the amino acid sequence of the light-chain FR3 is the amino acid sequence represented by SEQ ID NO: 13, and the amino acid sequence of the light-chain FR4 is the amino acid sequence represented by SEQ ID NO: 14.

In the amino acid sequence I, the amino acid sequences of the heavy-chain FRs 1 to 4 and the light-chain FRs 1 to 4 may have a sequence identity of not less than 90%, preferably not less than 95%, to the amino acid sequences represented by SEQ ID NOs: 7 to 14, respectively; in the amino acid sequence II, the amino acid sequences of the heavy-chain FRs 1 to 4 and the light-chain FRs 1 to 4 may have a sequence identity of not less than 90%, preferably not less than 95%, to the amino acid sequences represented by SEQ ID NOs: 7, 15, 16, 10 to 14, respectively. The details are described above.

Additionally, the anti-podoplanin antibody or antibody fragment containing the antigen-binding region thereof is also preferably a mouse-human chimeric antibody, as described above, as long as the effects of the present invention are achieved, in which the variable regions preferably comprise the following amino acid sequences, wherein the amino acid sequence of the heavy-chain CDR1 is the amino acid sequence represented by SEQ ID NO: 1, the amino acid sequence of the heavy-chain CDR2 is the amino acid sequence represented by SEQ ID NO: 2, the amino acid sequence of the heavy-chain CDR3 is the amino acid sequence represented by SEQ ID NO: 3, the amino acid sequence of the light-chain CDR1 is the amino acid sequence represented by SEQ ID NO: 4, the amino acid sequence of the light-chain CDR2 is the amino acid sequence represented by SEQ ID NO: 5, the amino acid sequence of the light-chain CDR3 is the amino acid sequence represented by SEQ ID NO: 6, the amino acid sequence of the heavy-chain FR1 is the amino acid sequence represented by SEQ ID NO: 17, the amino acid sequence of the heavy-chain FR2 is the amino acid sequence represented by SEQ ID NO: 18, the amino acid sequence of the heavy-chain FR3 is the amino acid sequence represented by SEQ ID NO: 19, the amino acid sequence of the heavy-chain FR4 is the amino acid sequence represented by SEQ ID NO: 20, the amino acid sequence of the light-chain FR1 is the amino acid sequence represented by SEQ ID NO: 21, the amino acid sequence of the light-chain FR2 is the amino acid sequence represented by SEQ ID NO: 22, the amino acid sequence of the light-chain FR3 is the amino acid sequence represented by SEQ ID NO: 23, and the amino acid sequence of the light-chain FR4 is the amino acid sequence represented by SEQ ID NO: 24.

The amino acid sequences of the heavy-chain FRs 1 to 4 and the light-chain FRs 1 to 4 may have a sequence identity of not less than 90%, preferably not less than 95%, to the amino acid sequences represented by SEQ ID NOs: 17 to 24, respectively. The details are described above.

An anti-podoplanin antibody or antibody fragment containing the antigen-binding region thereof according to the present invention can be produced based on the amino acid sequences, which collectively encode the structure of the anti-podoplanin antibody or antibody fragment containing the antigen-binding region thereof, by using any known genetic engineering technique.

Additionally, the production process may comprise the step of recovering an obtained anti-podoplanin antibody or an obtained antibody fragment containing the antigen-binding region thereof. The recovery step may be a purification step, a concentration step, or the like. In the purification step, any known purification technique may be used. The purification technique may be used to purify an anti-podoplanin antibody or antibody fragment containing the antigen-binding region thereof according to the present invention.

The anti-podoplanin antibody of the present invention includes a multispecific antibody, a functionally modified antibody, and a conjugated antibody. Known methods are included as the production methods for those antibodies.

Another aspect of the present invention is an agent for inhibiting the binding between podoplanin and CLEC-2 which comprises the anti-podoplanin antibody or antibody fragment containing the antigen-binding region thereof (hereinafter sometimes referred to, for example, as "the agent for inhibiting the binding according to the present aspect").

In addition, the agent for inhibiting the binding according to the present aspect may be a composition for inhibiting the binding. Additionally, the agent for inhibiting the binding according to the present aspect and the composition for inhibiting the binding may be mixtures, whose component compositions may be homogenous or heterogenous.

The agent for inhibiting the binding according to the present aspect acts to inhibit the binding between podoplanin and CLEC-2 and thus has effects obtained by inhibition of the binding between podoplanin and CLEC-2.

The agent for inhibiting the binding according to the present aspect may contain one or more kinds of anti-podoplanin antibodies as described above or antibody fragments containing the antigen-binding regions thereof.

The content of the anti-podoplanin antibody(ies) or the antibody fragment(s) containing the antigen-binding region(s) thereof in the agent for inhibiting the binding according to the present aspect is not specifically limited as long as the content is effective to inhibit the binding between podoplanin and CLEC-2, and the total content of the anti-podoplanin antibody(ies) or the antibody fragment(s) containing the antigen-binding region(s) thereof is normally not less than 0.5 mg/mL, preferably not less than 1 mg/mL, more preferably not less than 10 mg/mL, and is also normally not more than 500 mg/mL, preferably not more than 200 mg/mL, more preferably not more than 100 mg/mL.

Other details of the agent for inhibiting the binding according to the present aspect incorporate those described for the following "pharmaceutical composition which comprises the anti-podoplanin antibody or antibody fragment containing the antigen-binding region thereof."

Still another aspect of the present invention is a pharmaceutical composition which comprises the anti-podoplanin antibody or antibody fragment containing the antigen-binding region thereof (hereinafter sometimes referred to, for example, as "the pharmaceutical composition according to the present aspect").

The pharmaceutical composition according to the present aspect acts to inhibit the binding between podoplanin and CLEC-2 and thus has effects which are obtained by inhibition of the binding between podoplanin and CLEC-2. Examples of the effects include an effect to reduce proliferation or metastasis of cancer cells, an effect to inhibit platelet aggregation, an antithrombotic effect, and an anti-inflammatory effect. Accordingly, the pharmaceutical composition according to the present aspect can be used as, for example, a pharmaceutical composition intended for reducing the proliferation or metastasis of cancer cells and/or for inhibiting platelet aggregation, thrombosis, or inflammation.

The cancer cells are preferably podoplanin-positive tumor cells. Examples of the podoplanin-positive tumor cells include mesothelioma cells, brain tumor cells, testis tumor cells, Kaposi's sarcoma cells, lymphangioma cells, cavernous hemangioma cells, angiosarcoma cells, lung squamous cell carcinoma cells, ovarian dysgerminoma cells, glioma cells, germ cell tumor cells, head and neck cancer cells, lung cancer cells, bladder cancer cells, bone and soft tissue sarcoma cells (primary bone tumor (osteosarcoma, chondrosarcoma) cells, soft tissue sarcoma cells), and esophagus cancer cells.

Accordingly, the pharmaceutical composition according to the present aspect can be used for prevention or treatment of any disease that can be prevented or treated by reducing proliferation or metastasis of cancer cells and/or inhibiting platelet aggregation, thrombosis, or inflammation. The term "treatment" includes the meaning of amelioration. Examples of the disease include mesothelioma, brain tumor, testis tumor, Kaposi's sarcoma, lymphangioma, cavernous hemangioma, angiosarcoma, lung squamous cell carcinoma, ovarian dysgerminoma, glioma, germ cell tumor, head and neck cancer, lung cancer, bladder cancer, bone and soft tissue sarcoma (primary bone tumor (osteosarcoma, chondrosarcoma), soft tissue sarcoma), and esophagus cancer.

The pharmaceutical composition according to the present aspect contains an anti-podoplanin antibody(ies) as described above or an antibody fragment(s) containing the antigen-binding region(s) thereof. That is, the pharmaceutical composition according to the present aspect may contain one or more kinds of anti-podoplanin antibodies as described above or antibody fragments containing the antigen-binding regions thereof.

Administration of the pharmaceutical composition according to the present aspect is not limited to a particular administration mode, and the pharmaceutical composition can be administered orally or parenterally. Examples of parenteral administration include intravenous injection, intramuscular injection, subcutaneous administration, rectal administration, transdermal administration, intracerebral administration, intrathecal administration, and other topical administrations.

Dosage forms for oral and parenteral administrations, and methods for preparation of the dosage forms are well-known to those skilled in the art, under which the anti-podoplanin antibody or antibody fragment containing the antigen-binding region thereof can be combined with, for example, pharmaceutically acceptable carriers to produce a pharmaceutical composition.

Dosage forms for parenteral administration include, for example, formulation for injection, external preparation, suppository and inhalant, eye drop, eye ointment, nasal drop, ear drop, and liposome preparation.

Examples of formulations for injection include formulations for drip injection, formulations for intravenous injection, formulations for intramuscular injection, formulations for subcutaneous injection, formulations for intradermal injection, formulations for intracerebral administration, and formulations for intrathecal administration.

Examples of external preparations include ointments, poultices, and lotions.

Especially in cases where those dosage forms are directly applied to central nervous tissues, the dosage forms can be administered by sustained infusion using a medical micropump device with an osmotic pump, or can be mixed with, for example, fibrin glue to form a sustained-release formulation, which can be then applied to an affected tissue.

Among those dosage forms, a formulation for injection, for example, is usually prepared by dissolving an antibody of interest in distilled water for injection, to which a solubilizing agent, a buffering agent, a pH conditioner, a tonicity agent, a soothing agent, a preservative agent, a stabilizing agent, and the like can be added as necessary. Additionally, a lyophilized formulation for reconstitution is also feasible.

Dosage forms for oral administration include solid or liquid dosage forms and specifically include, for example, tablet, coated tablet, pill, fine granule, granule, powder, capsule, syrup, emulsion, suspension, formulation for injection, and troche.

The pharmaceutical composition according to the present aspect may further contain another therapeutically effective agent and also contain other components, such as an antimicrobial agent, an anti-inflammatory agent, vitamins, and amino acids, as necessary.

Examples of the pharmaceutically acceptable carriers include excipients, lubricants, binders, and disintegrating agents for solid formulations; or alternatively include solvents, solubilizing agents, suspending agents, tonicity agents, buffering agents, and soothing agents for liquid formulations.

Furthermore, proper amounts of commonly used additives, such as an antiseptic agent, an antioxidant, a coloring agent, a sweetening agent, an adsorbent, and a wetting agent, may be used appropriately as necessary.

The dosage of the pharmaceutical composition according to the present aspect is determined by a physician based on various factors including, for example, administration route, the type of disease, the seriousness of symptoms, the age, gender, and body weight of the patient, the severity of the disease, pharmacological properties such as pharmacokinetics and toxicological properties, use or non-use of a drug delivery system, and administration as a part of a combination regimen with other drugs.

The pharmaceutical composition according to the present aspect can be administered orally or parenterally. In the case of parenteral administration, the pharmaceutical composition can be administered by, for example but not limited to, intravenous infusion, subcutaneous infusion, intramuscular infusion, peritoneal infusion, intracutaneous administration, topical administration, nasal administration, intrapulmonary administration, and rectal administration. Although the dosage of the pharmaceutical composition is not specifically limited, the dosage is normally from about 0.01 µg/kg/day to about 1000 mg/kg/day, preferably about 0.01 mg/kg/day to about 100 mg/kg/day, further preferably about 0.1 mg/kg/day to about 20 mg/kg/day. The pharmaceutical composition can be administered at a frequency of, for example but not limited to, every day, once a week, one to four times a month, or one to seven times a year.

The pharmaceutical composition according to the present aspect may be administered alone or in combination with other pharmaceutical compositions or medicines, such as pharmaceutical compositions or medicines to prevent or treat mesothelioma, brain tumor, testis tumor, Kaposi's sarcoma, lymphangioma, cavernous hemangioma, angiosarcoma, lung squamous cell carcinoma, ovarian dysgerminoma, glioma, germ cell tumor, head and neck cancer, lung cancer, bladder cancer, bone and soft tissue sarcoma (primary bone tumor (osteosarcoma, chondrosarcoma), soft tissue sarcoma), and esophagus cancer.

Additionally, the present invention encompasses the following aspects.

[1] Use of the anti-podoplanin antibody or antibody fragment containing the antigen-binding region thereof, for producing an agent or composition for inhibiting the binding between podoplanin and CLEC-2.

[2] The anti-podoplanin antibody or antibody fragment containing the antigen-binding region thereof for use in preventing or treating a disease that can be prevented or treated by inhibiting the binding between podoplanin and CLEC-2.

[3] A method of preventing or treating a disease that can be prevented or treated by inhibiting the binding between podoplanin and CLEC-2, the method comprising administering a prophylactically or therapeutically effective amount of the anti-podoplanin antibody or antibody fragment containing the antigen-binding region thereof to a human subject or a patient in need thereof.

[4] Use of the anti-podoplanin antibody or antibody fragment containing the antigen-binding region thereof for inhibiting the binding between podoplanin and CLEC-2.

[5] The anti-podoplanin antibody or antibody fragment containing the antigen-binding region thereof for use in inhibiting the binding between podoplanin and CLEC-2.

[6] A method of inhibiting the binding between podoplanin and CLEC-2, the method comprising the step of administering (i) the anti-podoplanin antibody or antibody fragment containing the antigen-binding region thereof, (ii) the agent for inhibiting the binding between podoplanin and CLEC-2, or (iii) the composition for inhibiting the binding between podoplanin and CLEC-2, to a human subject.

Another aspect of the present invention is a DNA segment(s) encoding the protein moiety(ies) of the anti-podoplanin antibody or antibody fragment containing the antigen-binding region thereof. Those skilled in the art can readily design nucleotide sequences of the DNA segments encoding the protein moieties of the anti-podoplanin antibody, based on the amino acid sequences of the protein moieties. Specific examples of the nucleotide sequences include nucleotide sequences (SEQ ID NOs: 27 to 52) listed in Examples.

Additionally, a sequence coding for a signal peptide and/or the Kozak sequence may be added to the DNA segment(s) according to the present aspect.

The DNA segment according to the present aspect can be synthesized using known genetic engineering techniques.

Still another aspect of the present invention is a recombinant vector comprising the DNA segment(s).

The recombinant vector according to the present aspect may be based on any known vector, including plasmid vectors and viral vectors. The vector is preferably a vector that enables gene expression in eukaryotic cells, more preferably a vector that enables gene expression in mammalian cells, though the vector may be a vector that enables gene expression in prokaryotic cells, such as *Escherichia coli* cells.

Yet another aspect of the present invention is a host cell (transformant) comprising the DNA segment(s) or the recombinant vector.

The host cells according to the present aspect are host cells can be transfected or transformed with the DNA segment(s) or the recombinant vector. The host cells according to the present aspect may be based on any known cells. The cells are preferably eukaryotic cells, more preferably mammalian cells, though the cells may be prokaryotic cells, such as *Escherichia coli* and *Bacillus subtilis* cells.

Examples of the host cells include CHO cells, such as CHO-S cells as a CHO cell's lineage, and examples of a vector that enables gene expression in the cells include Freedom® pCHO 1.0 (Thermo Fisher Scientific).

EXAMPLES

Now, the present invention will be specifically described by way of examples, but the present invention is not limited to those examples.

Example 1: Determination of the Amino Acid Sequence of a Humanized Anti-Podoplanin Antibody In order to modify the mouse antibody PG4D2 to produce a humanized antibody, the CDRs and FRs of the heavy and light chains of the mouse antibody PG4D2 were determined using the antibody databases IMGT and Abysis, according to the Kabat numbering system. Next, the IMGT database was used to select human germline (germ cell line, GL) FR sequences for both chains, which are highly identical to the above amino acid sequences, from heavy-chain and light-chain FR sequences. FR sequences sharing the highest amino acid identities with the FRs 1 to 4 were selected by using a FR shuffling approach to determine an optimal combination of FRs 1 to 4. The complementarity-determining regions from the mouse antibody PG4D2 were grafted onto the selected human germline FRs for both of the heavy and light chains to design candidate sequences for the humanized antibody. Furthermore, the amino acid sequences of two humanized antibodies K4 and K5 were determined according to the following criteria: whether or not all of specified amino acid residues are fully conserved; whether or not the isoelectronic points (pIs) of the FRs are significantly high; whether or not the frequencies of use of the selected GL FR sequences are significantly low; whether or not any chemical modification site is present; whether or not unconserved amino acid residues, which are identified by comparison to the mouse antibody PG4D2, have two or more different properties from their counterparts in the mouse antibody in terms of three properties: side-chain hydrophobicity, volume, and physicochemical property; whether or not the amino acid sequences share high identities; and the like. That is, neither the humanized antibodies K4 nor K5 is an antibody that can be obtained by simply substituting the FRs from both the heavy and light chains of the mouse antibody PG4D2 with those from a human antibody.

Production Example 1: Production of a Humanized Anti-Podoplanin Antibody

The amino acid sequences of the resulting humanized antibodies K4 and K5 are presented below.

In the amino acid sequence of the humanized antibody K4, the variable regions comprise the heavy-chain CDR1 comprising the amino acid sequence represented by SEQ ID NO: 1, the heavy-chain CDR2 comprising the amino acid sequence represented by SEQ ID NO: 2, the heavy-chain CDR3 comprising the amino acid sequence represented by SEQ ID NO: 3, the light-chain CDR1 comprising the amino acid sequence represented by SEQ ID NO: 4, the light-chain CDR2 comprising the amino acid sequence represented by SEQ ID NO: 5, the light-chain CDR3 comprising the amino acid sequence represented by SEQ ID NO: 6, the heavy-chain FR1 comprising the amino acid sequence represented by SEQ ID NO: 7, the heavy-chain FR2 comprising the amino acid sequence represented by SEQ ID NO: 8, the heavy-chain FR3 comprising the amino acid sequence represented by SEQ ID NO: 9, the heavy-chain FR4 comprising the amino acid sequence represented by SEQ ID NO: 10, the light-chain FR1 comprising the amino acid sequence represented by SEQ ID NO: 11, the light-chain FR2 comprising the amino acid sequence represented by SEQ ID NO: 12, the light-chain FR3 comprising the amino acid sequence represented by SEQ ID NO: 13, and the light-chain FR4 comprising the amino acid sequence represented by SEQ ID NO: 14, and the constant regions comprise the amino acid sequences of those from a human antibody of the IgG4 subclass, in which the amino acid sequence of the heavy-chain constant region is the amino acid sequence represented by SEQ ID NO: 25 and the amino acid sequence of the light-chain constant region is the amino acid sequence represented by SEQ ID NO: 26.

In the amino acid sequence of the humanized antibody K5, the variable regions comprise the heavy-chain CDR1 comprising the amino acid sequence represented by SEQ ID NO: 1, the heavy-chain CDR2 comprising the amino acid sequence represented by SEQ ID NO: 2, the heavy-chain CDR3 comprising the amino acid sequence represented by SEQ ID NO: 3, the light-chain CDR1 comprising the amino acid sequence represented by SEQ ID NO: 4, the light-chain CDR2 comprising the amino acid sequence represented by SEQ ID NO: 5, the light-chain CDR3 comprising the amino acid sequence represented by SEQ ID NO: 6, the heavy-chain FR1 comprising the amino acid sequence represented by SEQ ID NO: 7, the heavy-chain FR2 comprising the amino acid sequence represented by SEQ ID NO: 15, the heavy-chain FR3 comprising the amino acid sequence represented by SEQ ID NO: 16, the heavy-chain FR4 comprising the amino acid sequence represented by SEQ ID NO: 10, the light-chain FR1 comprising the amino acid sequence represented by SEQ ID NO: 11, the light-chain FR2 comprising the amino acid sequence represented by SEQ ID NO: 12, the light-chain FR3 comprising the amino acid sequence represented by SEQ ID NO: 13, the light-chain FR4 comprising the amino acid sequence represented by SEQ ID NO: 14, and the constant regions comprise the same amino acid sequences as those of the above-described humanized antibody K4.

Additionally, the following nucleotide sequences were used as nucleotide sequences encoding the above-described amino acid sequences.

The nucleotide sequences represented by SEQ ID NOs: 27 to 42 were used as nucleotide sequences encoding the amino acid sequences represented by SEQ ID NOs: 1 to 16, respectively.

The nucleotide sequence represented by SEQ ID NO: 43 was used as a nucleotide sequence encoding the amino acid sequence represented by SEQ ID NO: 25 (heavy-chain constant region), and the nucleotide sequence represented by SEQ ID NO: 44 was used as a nucleotide sequence encoding the amino acid sequence represented by SEQ ID NO: 26 (light-chain constant region).

The Freedom® pCHO 1.0 vector (Thermo Fisher Scientific) was used for gene expression in CHO cells (Thermo Fisher Scientific) as an expression vector.

CHO cells expressing either the humanized antibody K4 or K5 were thawed and then eventually amplified in a 10-L stirred bioreactor in a fed-batch mode under the following culture conditions: a stirring rate of 100 rpm, a culture temperature of 37° C., and a pH of 7.0. The culture was collected after 6 to 8 days of incubation.

The collected cultures were used to purify and obtain the humanized antibodies K4 and K5. The collected culture supernatants were used for the measurements described in Examples 2 and 3 below.

Production Example 2: Production of a Mouse-Human Chimeric Anti-Podoplanin Antibody The amino acid sequence of the mouse-human chimeric antibody chPG4D2 is presented below.

In the amino acid sequence of the mouse-human chimeric antibody chPG4D2, the variable regions comprise the heavy-chain CDR1 comprising the amino acid sequence represented by SEQ ID NO: 1, the heavy-chain CDR2 comprising the amino acid sequence represented by SEQ ID NO: 2, the heavy-chain CDR3 comprising the amino acid sequence represented by SEQ ID NO: 3, the light-chain CDR1 comprising the amino acid sequence represented by SEQ ID NO: 4, the light-chain CDR2 comprising the amino acid sequence represented by SEQ ID NO: 5, the light-chain CDR3 comprising the amino acid sequence represented by SEQ ID NO: 6, the heavy-chain FR1 comprising the amino acid sequence represented by SEQ ID NO: 17, the heavy-chain FR2 comprising the amino acid sequence represented by SEQ ID NO: 18, the heavy-chain FR3 comprising the amino acid sequence represented by SEQ ID NO: 19, the heavy-chain FR4 comprising the amino acid sequence represented by SEQ ID NO: 20, the light-chain FR1 comprising the amino acid sequence represented by SEQ ID NO: 21, the light-chain FR2 comprising the amino acid sequence represented by SEQ ID NO: 22, the light-chain FR3 comprising the amino acid sequence represented by SEQ ID NO: 23, the light-chain FR4 comprising the amino acid sequence represented by SEQ ID NO: 24, and the constant regions comprise the same amino acid sequences as those of the above-described humanized antibody K4.

Those skilled in the art can readily understand that the mouse-human chimeric antibody chPG4D2 can be produced in the same manner as in Production Example 1 by designing nucleotide sequences encoding the above-described amino acid sequences represented by SEQ ID NOs: 1 to 6 and 17 to 24 and the constant regions of the above described humanized antibody K4.

In this case, for example, the following nucleotide sequences can be used as nucleotide sequences encoding the above-described amino acid sequences.

The nucleotide sequences represented by SEQ ID NOs: 27 to 32 and 45 to 52 can be used as nucleotide sequences encoding the amino acid sequences represented by SEQ ID NOs: 1 to 6 and 17 to 24, respectively.

The same nucleotide sequences encoding the amino acid sequences of the constant regions as those described in Production Example 1 can be used.

The Freedom® pCHO 1.0 vector (Thermo Fisher Scientific) was used for gene expression in CHO cells (Thermo Fisher Scientific) as an expression vector.

CHO cells expressing the mouse-human chimeric antibody chPG4D2 were thawed and then eventually amplified in a 5-L stirred bioreactor in a batch mode under the following culture conditions: a stirring rate of 100 rpm, a culture temperature of 37° C., and a pH of 7.0. The culture was collected after 7 days of incubation.

The collected culture was used to purify and obtain the mouse-human chimeric antibody chPG4D2. The collected culture supernatant was used for the measurements described in Examples 2 and 3 below.

Example 2: Podoplanin-Binding Activity of Each Antibody

The culture supernatants collected in Production Examples 1 and 2 were used to measure the binding activity to the podoplanin PLAG4 domain, following the ELISA protocol described in Patent Document 1. A peptide of the human podoplanin PLAG4 domain (WT-hPLAG4 (Genscript, 788349-1)) as an antigen peptide was immobilized on a solid phase, and a preadsorbed goat biotin-conjugated anti-human IgG Fc antibody (Abcam, ab98618) and β-Gal-conjugated streptavidin (Roche Diagnostics, 11112481001) were used for a detection purpose.

The result is presented in Table 1. The avidity (antibody titer) of each antibody was expressed relative to that of the mouse-human chimeric antibody chPG4D2, which is set as 100%.

TABLE 1

| Antibody | Avidity (antibody titer) (%) |
| --- | --- |
| Humanized antibody K4 | 84.8 to 171.8 |
| Humanized antibody K5 | 90.0 to 111.5 |
| Mouse-human chimeric antibody chPG4D2 | 100 |

Example 3: Inhibitory Activity of Each Antibody Against Binding of Podoplanin to CLEC-2

The culture supernatants collected in Production Examples 1 and 2 were used to measure the inhibitory activity against binding of podoplanin to CLEC-2, following the ELISA protocol described in Patent Document 1. A recombinant human CLEC-2 (R&D, 1718-CL-050) as an antigen peptide was immobilized on a solid phase, and a recombinant human podoplanin Fc chimera protein (R&D, 3670-PL) was used as a protein capable of binding to the above recombinant human CLEC-2, and a preadsorbed goat biotin-conjugated anti-human IgG Fc antibody (Abcam, ab98618) and β-Gal-conjugated streptavidin (SIGMA, 53887; Roche, 11112481001) were used for a detection purpose.

The mouse antibody PG4D2 (PG4D2) was used as a positive control. The mouse antibody PG4D2 is a monoclonal antibody that is obtained from the NITE P-02071 (PG4D2) hybridoma.

The result is presented in Table 2.

TABLE 2

| Antibody | $IC_{50}$ (ng/mL) | Mode of inhibition |
|---|---|---|
| Humanized antibody K4 | 360 | Complete inhibition |
| Humanized antibody K5 | 364 | Complete inhibition |
| Mouse-human chimeric antibody chPG4D2 | 406 | Complete inhibition |
| Mouse antibody PG4D2 (PG4D2) | 371 ± 14 (mean ± SD) | Complete inhibition |

Example 4: In Vitro Inhibitory Effect of Each Antibody on Platelet Aggregation It has been reported that introduction of the human podoplanin gene into CHO cells results in the induction of platelet aggregation, though normal CHO cells do not induce platelet aggregation (J. Biol. Chem., December 19; 278(51): 51599-605 (2003)).

The ability of each antibody to inhibit platelet aggregation was analyzed using a whole blood aggregometer WBA-CARNA (TAIYO Instruments) in aliquots of human whole blood combined with cells of the human podoplanin-positive osteosarcoma cell line SJSA-1 (ATCC® CRL-2098) to induce platelet aggregation. The osteosarcoma cell line SJSA-1 (ATCC® CRL-2098) is available from the American Type Culture Collection (address: 12301 Parklawn Drive, Rockville, Md. 20852, United States of America). ATCC is a registered trademark of the American Type Culture Collection. ATCC® is used to indicate that the specific cell line identified is also a trademark of the American Type Culture Collection.

A human antibody of the IgG4 subclass (CrownBio, C0004) was used as a negative control in the assay using the humanized antibody K4 or K5.

In this in vitro assay, the whole blood, which contains aggregates induced by the cells, is sucked through a micromesh filter and an increase in suction pressure due to clogging by the aggregates is measured to calculate the aggregation rate.

The mouse antibody PG4D2 (PG4D2) was used as a positive control. Additionally, a mouse antibody of the IgG2a subclass (Sigma, M9144) was used as a negative control in a system using the mouse antibody PG4D2.

Figure 2:
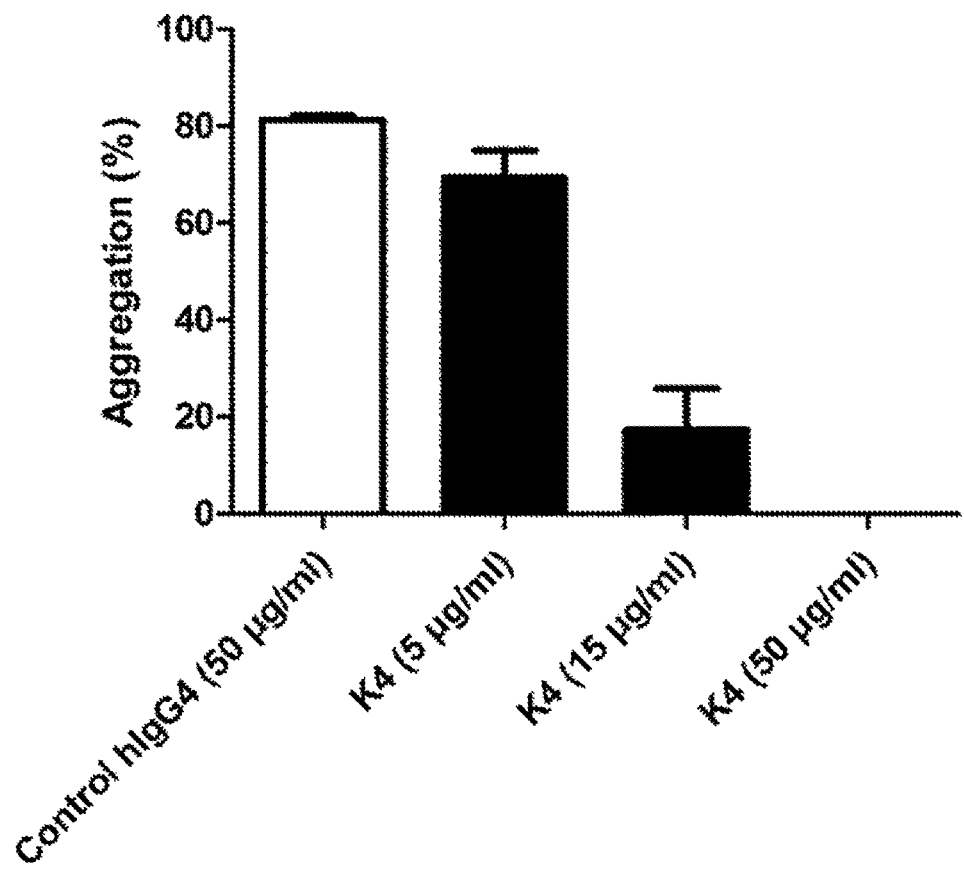
FIG. 2 shows the inhibitory effect of the humanized antibody K4 on in vitro platelet aggregation in an example of the present invention.
Figure 3:
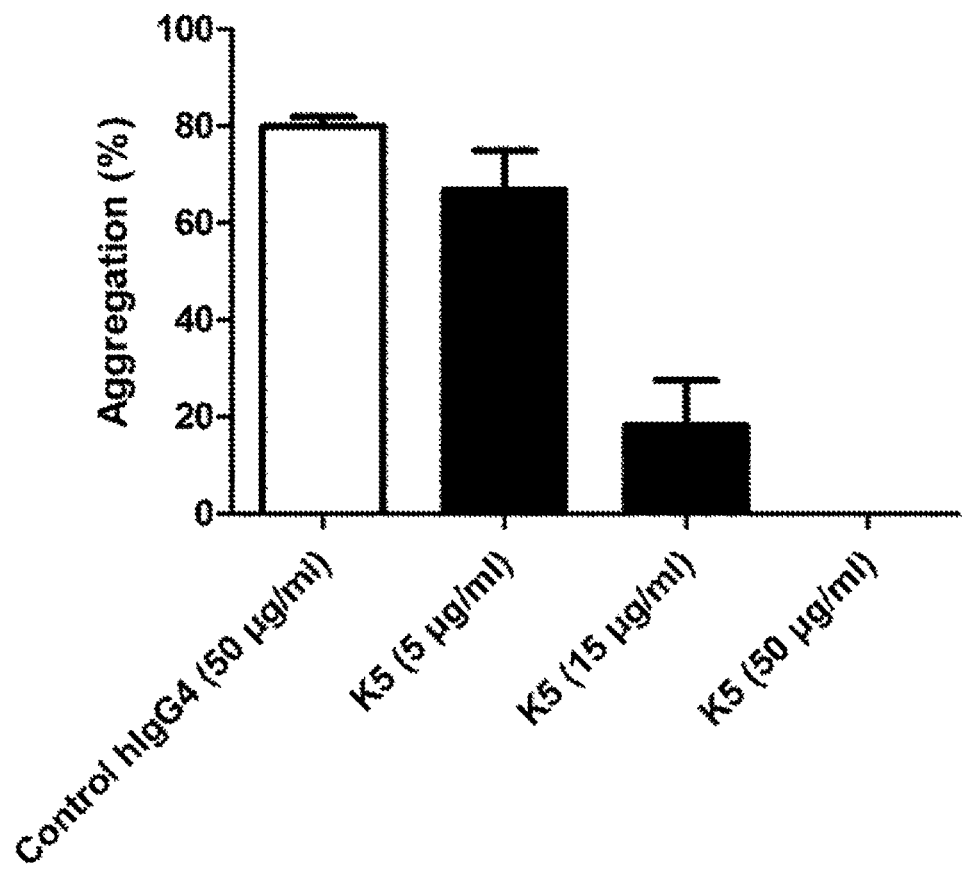
FIG. 3 shows the inhibitory effect of the humanized antibody K5 on in vitro platelet aggregation in an example of the present invention.

The results are shown in FIGS. 1 to 3. The humanized antibodies K4 and K5 inhibited platelet aggregation in a concentration-dependent manner, as seen for the positive control.

Example 5: Inhibitory Effect of Each Antibody on Hematogenous Metastasis to Lung A hematogenous metastasis model was used to analyze the inhibitory effect of each antibody on hematogenous metastasis, in which the human podoplanin-positive osteosarcoma cell line SJSA-1 (ATCC® CRL-2098) were injected into severe combined immunodeficient (SCID-Beige) mice (CB17.Cg-Prkdc$^{scid}$Lyst$^{bg-J}$/CrlCrlj; Charles River Laboratories Japan; female, six weeks old) via tail vein and the number of metastatic nodules formed on the lung surface was counted 20 days later.

The control antibody (the human antibody of the IgG4 subclass (CrownBio)), the humanized antibody K4, and the humanized antibody K5 were individually administered to groups, each consisting of 6 mice, via the tail vein route on the day before SJSA-1 cell injection to study the effect of podoplanin on experimental lung metastasis.

Figure 4:
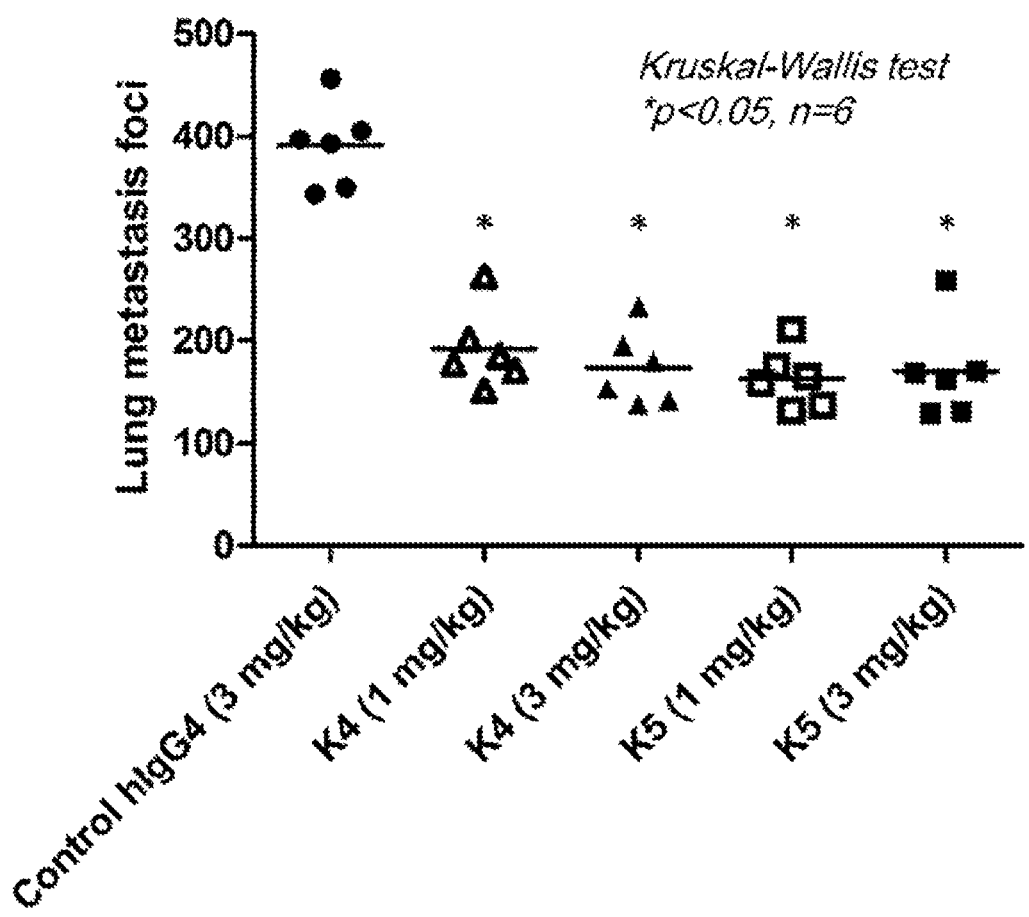
FIG. 4 shows the inhibitory effect of either the humanized antibody K4 or K5 on hematogenous metastasis to lung in an example of the present invention.

The result is shown in FIG. 4. Preliminary administration of the humanized antibody K4 or K5 significantly inhibited metastasis of SJSA-1 cells to the lung.

Example 6: Antitumor Effect of Each Antibody $5 \times 10^6$ cells of the human podoplanin-positive osteosarcoma cell line SJSA-1 (ATCC® CRL-2098) were inoculated subcutaneously to each of severe combined immunodeficient (SCID-Beige) mice (CB17.Cg-Prkdc$^{scid}$Lyst$^{bg-J}$/CrlCrlj; Charles River Laboratories Japan; female, five weeks old) to generate xenograft model mice, and the in vivo antitumor effects of the humanized antibodies K4 and K5 were examined in the xenograft model mice.

The humanized antibodies K4 and K5 were administered to the K4-dosed and K5-dosed groups of mice, respectively, at a frequency of twice a week from Day 1 (Day 1, Day 4, Day 8, Day 11, and Day 15) and at a dose of 5 mg/kg. Tumor size (½×length×(width)$^2$) and body weight were measured twice a week (n=6). Photographs were taken and excised tumors were weighed at endpoint (20 days after inoculation).

A human antibody of the IgG4 subclass (Sino Biological, HG4K) was used as a negative control.

Figure 5:
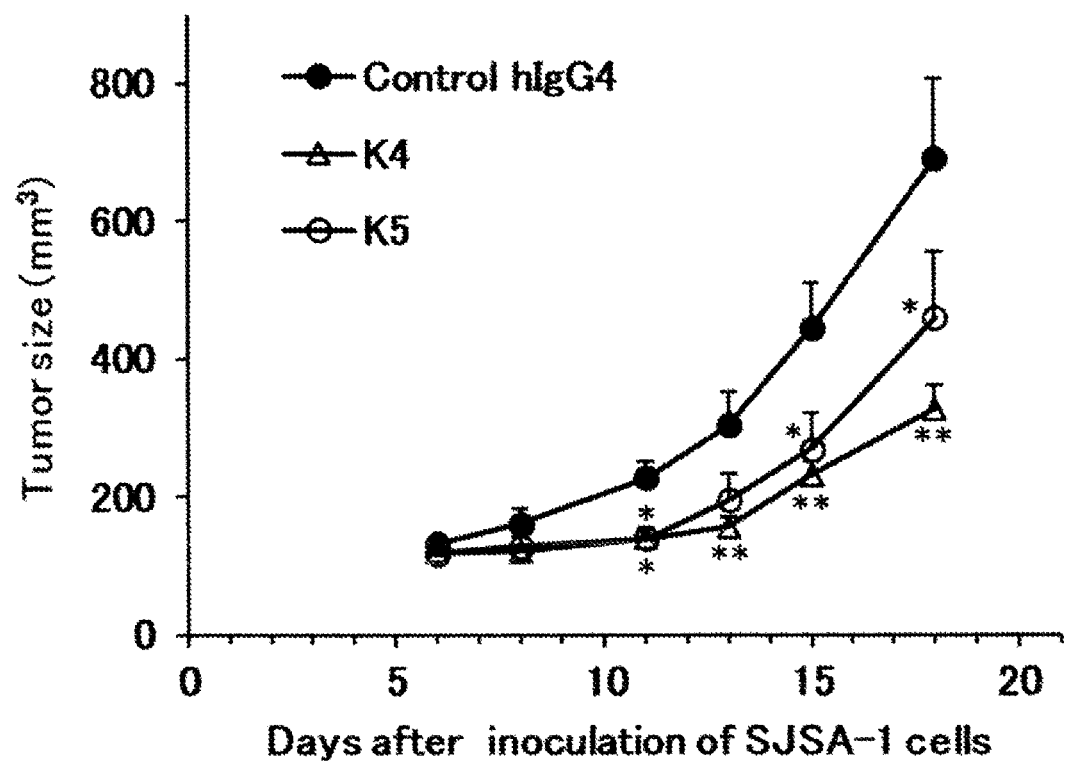
FIG. 5 shows the anti-tumor effect of either the humanized antibody K4 or K5 in an example of the present invention.

The result (the relationship between days after inoculation and mean tumor size) is shown in FIG. 5 (* $p<0.05$, ** $p<0.01$, Kruskal-Wallis test). An inhibitory effect on tumor proliferation was observed in each of the K4-dosed and K5-dosed groups. No significant body weight loss was observed in any group of mice during the study.

The invention claimed is:

1. An isolated humanized anti-podoplanin antibody, or an antibody fragment thereof, comprising an antigen-binding region, which comprises a variable region comprising the amino acid sequence I or II below, the amino acid sequences of the heavy-chain FRs 1 to 4 and the light-chain FRs 1 to 4 in the following amino acid sequence I optionally have a sequence identity of not less than 90% to the amino acid sequences represented by SEQ ID NOs: 7 to 14 below, respectively, and
the amino acid sequences of the heavy-chain FRs 1 to 4 and the light-chain FRs 1 to 4 in the following amino acid sequence II optionally have a sequence identity of not less than 90% to the amino acid sequences represented by SEQ ID NOs: 7, 15, 16, 10 to 14 below, respectively;
wherein, in the amino acid sequence I,
the amino acid sequence of the heavy-chain CDR1 is the amino acid sequence represented by SEQ ID NO: 1,
the amino acid sequence of the heavy-chain CDR2 is the amino acid sequence represented by SEQ ID NO: 2,
the amino acid sequence of the heavy-chain CDR3 is the amino acid sequence represented by SEQ ID NO: 3,
the amino acid sequence of the light-chain CDR1 is the amino acid sequence represented by SEQ ID NO: 4,
the amino acid sequence of the light-chain CDR2 is the amino acid sequence represented by SEQ ID NO: 5,
the amino acid sequence of the light-chain CDR3 is the amino acid sequence represented by SEQ ID NO: 6,
the amino acid sequence of the heavy-chain FR1 is the amino acid sequence represented by SEQ ID NO: 7,
the amino acid sequence of the heavy-chain FR2 is the amino acid sequence represented by SEQ ID NO: 8,
the amino acid sequence of the heavy-chain FR3 is the amino acid sequence represented by SEQ ID NO: 9,
the amino acid sequence of the heavy-chain FR4 is the amino acid sequence represented by SEQ ID NO: 10,
the amino acid sequence of the light-chain FR1 is the amino acid sequence represented by SEQ ID NO: 11,
the amino acid sequence of the light-chain FR2 is the amino acid sequence represented by SEQ ID NO: 12,
the amino acid sequence of the light-chain FR3 is the amino acid sequence represented by SEQ ID NO: 13, and
the amino acid sequence of the light-chain FR4 is the amino acid sequence represented by SEQ ID NO: 14; and
wherein, in the amino acid sequence II
the amino acid sequence of the heavy-chain CDR1 is the amino acid sequence represented by SEQ ID NO: 1,
the amino acid sequence of the heavy-chain CDR2 is the amino acid sequence represented by SEQ ID NO: 2,
the amino acid sequence of the heavy-chain CDR3 is the amino acid sequence represented by SEQ ID NO: 3,
the amino acid sequence of the light-chain CDR1 is the amino acid sequence represented by SEQ ID NO: 4,
the amino acid sequence of the light-chain CDR2 is the amino acid sequence represented by SEQ ID NO: 5,
the amino acid sequence of the light-chain CDR3 is the amino acid sequence represented by SEQ ID NO: 6,
the amino acid sequence of the heavy-chain FR1 is the amino acid sequence represented by SEQ ID NO: 7,
the amino acid sequence of the heavy-chain FR2 is the amino acid sequence represented by SEQ ID NO: 15,
the amino acid sequence of the heavy-chain FR3 is the amino acid sequence represented by SEQ ID NO: 16,
the amino acid sequence of the heavy-chain FR4 is the amino acid sequence represented by SEQ ID NO: 10,
the amino acid sequence of the light-chain FR1 is the amino acid sequence represented by SEQ ID NO: 11,
the amino acid sequence of the light-chain FR2 is the amino acid sequence represented by SEQ ID NO: 12, the amino acid sequence of the light-chain FR3 is the amino acid sequence represented by SEQ ID NO: 13, and
the amino acid sequence of the light-chain FR4 is the amino acid sequence represented by SEQ ID NO: 14,
wherein said anti-podoplanin antibody and antigen-binding region thereof specifically bind to the PLAG4 domain of human podoplanin.

2. The isolated humanized anti-podoplanin antibody or antibody fragment thereof, containing the antigen-binding region thereof according to claim 1, wherein the anti-podoplanin antibody comprises a constant region of a human antibody of the IgG class.

3. An isolated mouse-human chimeric anti-podoplanin antibody, or an antibody fragment thereof, comprising an antigen-binding region, which comprises variable regions comprising the following amino acid sequences,
the amino acid sequences of the heavy-chain FRs 1 to 4 and the light-chain FRs 1 to 4 optionally have a sequence identity of not less than 90% to the amino acid sequences represented by SEQ ID NO: 17 to 24 below, respectively,
wherein
the amino acid sequence of the heavy-chain CDR1 is the amino acid sequence represented by SEQ ID NO: 1,
the amino acid sequence of the heavy-chain CDR2 is the amino acid sequence represented by SEQ ID NO: 2,
the amino acid sequence of the heavy-chain CDR3 is the amino acid sequence represented by SEQ ID NO: 3,
the amino acid sequence of the light-chain CDR1 is the amino acid sequence represented by SEQ ID NO: 4,
the amino acid sequence of the light-chain CDR2 is the amino acid sequence represented by SEQ ID NO: 5,
the amino acid sequence of the light-chain CDR3 is the amino acid sequence represented by SEQ ID NO: 6,
the amino acid sequence of the heavy-chain FR1 is the amino acid sequence represented by SEQ ID NO: 17,
the amino acid sequence of the heavy-chain FR2 is the amino acid sequence represented by SEQ ID NO: 18,
the amino acid sequence of the heavy-chain FR3 is the amino acid sequence represented by SEQ ID NO: 19,
the amino acid sequence of the heavy-chain FR4 is the amino acid sequence represented by SEQ ID NO: 20,
the amino acid sequence of the light-chain FR1 is the amino acid sequence represented by SEQ ID NO: 21,
the amino acid sequence of the light-chain FR2 is the amino acid sequence represented by SEQ ID NO: 22,
the amino acid sequence of the light-chain FR3 is the amino acid sequence represented by SEQ ID NO: 23, and
the amino acid sequence of the light-chain FR4 is the amino acid sequence represented by SEQ ID NO: 24,
wherein said anti-podoplanin antibody and antigen-binding region thereof specifically bind to the PLAG4 domain of human podoplanin.

4. The isolated mouse-human chimeric anti-podoplanin antibody or antibody fragment thereof, comprising an anti-gen-binding region thereof according to claim 3, wherein the anti-podoplanin antibody comprises a constant region of a human antibody of the IgG class.

5. A method of inhibiting the binding between podoplanin and CLEC-2, the method comprising the step of administering
an isolated humanized anti-podoplanin antibody, or an antibody fragment thereof, comprising an antigen-binding region which comprises a variable region comprising the amino acid sequence I or II below, the amino acid sequences of the heavy-chain FRs 1 to 4 and the light-chain FRs 1 to 4 in the following amino acid sequence I optionally have a sequence identity of not less than 90% to the amino acid sequences represented by SEQ ID NOs: 7 to 14 below, respectively, and
the amino acid sequences of the heavy-chain FRs 1 to 4 and the light-chain FRs 1 to 4 in the following amino acid sequence II optionally have a sequence identity of not less than 90% to the amino acid sequences represented by SEQ ID NOs: 7, 15, 16, 10 to 14 below, respectively;
wherein in the amino acid sequence I,
the amino acid sequence of the heavy-chain CDR1 is the amino acid sequence represented by SEQ ID NO: 1,
the amino acid sequence of the heavy-chain CDR2 is the amino acid sequence represented by SEQ ID NO: 2,
the amino acid sequence of the heavy-chain CDR3 is the amino acid sequence represented by SEQ ID NO: 3,
the amino acid sequence of the light-chain CDR1 is the amino acid sequence represented by SEQ ID NO: 4,
the amino acid sequence of the light-chain CDR2 is the amino acid sequence represented by SEQ ID NO: 5,
the amino acid sequence of the light-chain CDR3 is the amino acid sequence represented by SEQ ID NO: 6,
the amino acid sequence of the heavy-chain FR1 is the amino acid sequence represented by SEQ ID NO: 7,
the amino acid sequence of the heavy-chain FR2 is the amino acid sequence represented by SEQ ID NO: 8,
the amino acid sequence of the heavy-chain FR3 is the amino acid sequence represented by SEQ ID NO: 9,
the amino acid sequence of the heavy-chain FR4 is the amino acid sequence represented by SEQ ID NO: 10,
the amino acid sequence of the light-chain FR1 is the amino acid sequence represented by SEQ ID NO: 11,
the amino acid sequence of the light-chain FR2 is the amino acid sequence represented by SEQ ID NO: 12,
the amino acid sequence of the light-chain FR3 is the amino acid sequence represented by SEQ ID NO: 13, and
the amino acid sequence of the light-chain FR4 is the amino acid sequence represented by SEQ ID NO: 14; and
wherein, in the amino acid sequence II,
the amino acid sequence of the heavy-chain CDR1 is the amino acid sequence represented by SEQ ID NO: 1,
the amino acid sequence of the heavy-chain CDR2 is the amino acid sequence represented by SEQ ID NO: 2,
the amino acid sequence of the heavy-chain CDR3 is the amino acid sequence represented by SEQ ID NO: 3,
the amino acid sequence of the light-chain CDR1 is the amino acid sequence represented by SEQ ID NO: 4,
the amino acid sequence of the light-chain CDR2 is the amino acid sequence represented by SEQ ID NO: 5,
the amino acid sequence of the light-chain CDR3 is the amino acid sequence represented by SEQ ID NO: 6,
the amino acid sequence of the heavy-chain FR1 is the amino acid sequence represented by SEQ ID NO: 7,
the amino acid sequence of the heavy-chain FR2 is the amino acid sequence represented by SEQ ID NO: 15,
the amino acid sequence of the heavy-chain FR3 is the amino acid sequence represented by SEQ ID NO: 16,
the amino acid sequence of the heavy-chain FR4 is the amino acid sequence represented by SEQ ID NO: 10,
the amino acid sequence of the light-chain FRI is the amino acid sequence represented by SEQ ID NO: 11,
the amino acid sequence of the light-chain FR2 is the amino acid sequence represented by SEQ ID NO: 12,
the amino acid sequence of the light-chain FR3 is the amino acid sequence represented by SEQ ID NO: 13, and
the amino acid sequence of the light-chain FR4 is the amino acid sequence represented by SEQ ID NO: 14,
to a human subject,
wherein said anti-podoplanin antibody and antigen-binding region thereof specifically bind to the PLAG4 domain of human podoplanin.

6. A pharmaceutical composition, comprising, an effective amount for specifically binding to podoplanin of an isolated humanized anti-podoplanin antibody or an antibody fragment thereof, containing an antigen-binding region which comprises a variable region comprising the amino acid sequence I or II below,
the amino acid sequences of the heavy-chain FRs 1 to 4 and the light-chain FRs 1 to 4 in the following amino acid sequence I optionally have a sequence identity of not less than 90% to the amino acid sequences represented by SEQ ID NOs: 7 to 14 below, respectively, and
the amino acid sequences of the heavy-chain FRs 1 to 4 and the light-chain FRs 1 to 4 in the following amino acid sequence II optionally have a sequence identity of not less than 90% to the amino acid sequences represented by SEQ ID NOs: 7, 15, 16, 10 to 14 below, respectively;
wherein in the amino acid sequence I,
the amino acid sequence of the heavy-chain CDR1 is the amino acid sequence represented by SEQ ID NO: 1,
the amino acid sequence of the heavy-chain CDR2 is the amino acid sequence represented by SEQ ID NO: 2,
the amino acid sequence of the heavy-chain CDR3 is the amino acid sequence represented by SEQ ID NO: 3,
the amino acid sequence of the light-chain CDR1 is the amino acid sequence represented by SEQ ID NO: 4,
the amino acid sequence of the light-chain CDR2 is the amino acid sequence represented by SEQ ID NO: 5,
the amino acid sequence of the light-chain CDR3 is the amino acid sequence represented by SEQ ID NO: 6,
the amino acid sequence of the heavy-chain FR1 is the amino acid sequence represented by SEQ ID NO: 7,
the amino acid sequence of the heavy-chain FR2 is the amino acid sequence represented by SEQ ID NO: 8,
the amino acid sequence of the heavy-chain FR3 is the amino acid sequence represented by SEQ ID NO: 9,
the amino acid sequence of the heavy-chain FR4 is the amino acid sequence represented by SEQ ID NO: 10,
the amino acid sequence of the light-chain FRI is the amino acid sequence represented by SEQ ID NO: 11,
the amino acid sequence of the light-chain FR2 is the amino acid sequence represented by SEQ ID NO: 12,
the amino acid sequence of the light-chain FR3 is the amino acid sequence represented by SEQ ID NO: 13, and
the amino acid sequence of the light-chain FR4 is the amino acid sequence represented by SEQ ID NO: 14; and
wherein, in the amino acid sequence II,
the amino acid sequence of the heavy-chain CDR1 is the amino acid sequence represented by SEQ ID NO: 1,
the amino acid sequence of the heavy-chain CDR2 is the amino acid sequence represented by SEQ ID NO: 2,
the amino acid sequence of the heavy-chain CDR3 is the amino acid sequence represented by SEQ ID NO: 3,
the amino acid sequence of the light-chain CDR1 is the amino acid sequence represented by SEQ ID NO: 4, the amino acid sequence of the light-chain CDR2 is the amino acid sequence represented by SEQ ID NO: 5,
the amino acid sequence of the light-chain CDR3 is the amino acid sequence represented by SEQ ID NO: 6,
the amino acid sequence of the heavy-chain FR1 is the amino acid sequence represented by SEQ ID NO: 7,
the amino acid sequence of the heavy-chain FR2 is the amino acid sequence represented by SEQ ID NO: 15,
the amino acid sequence of the heavy-chain FR3 is the amino acid sequence represented by SEQ ID NO: 16,
the amino acid sequence of the heavy-chain FR4 is the amino acid sequence represented by SEQ ID NO: 10,
the amino acid sequence of the light-chain FRI is the amino acid sequence represented by SEQ ID NO: 11,
the amino acid sequence of the light-chain FR2 is the amino acid sequence represented by SEQ ID NO: 12,
the amino acid sequence of the light-chain FR3 is the amino acid sequence represented by SEQ ID NO: 13, and
the amino acid sequence of the light-chain FR4 is the amino acid sequence represented by SEQ ID NO: 14;
and a pharmaceutically acceptable carrier,
wherein said anti-podoplanin antibody and antigen-binding region thereof specifically bind to the PLAG4 domain of human podoplanin.

7. The pharmaceutical composition according to claim 6, wherein said isolated humanized anti-podoplanin antibody, or an antibody fragment thereof is present in a therapeutically effective amount effective to inhibit the binding between podoplanin and CLEC-2.

8. The pharmaceutical composition according to claim 7, wherein said isolated humanized anti-podoplanin antibody, or an antibody fragment thereof is present in a therapeutically effective amount effective to inhibit platelet aggregation.

9. A method of inhibiting the binding between podoplanin and CLEC-2, the method comprising the step of administering
an isolated mouse-human chimeric anti-podoplanin antibody, or an antibody fragment thereof, comprising an antigen-binding region, which comprises variable regions comprising the following amino acid sequences,
the amino acid sequences of the heavy-chain FRs 1 to 4 and the light-chain FRs 1 to 4 optionally have a sequence identity of not less than 90% to the amino acid sequences represented by SEQ ID NO: 17 to 24 below, respectively,
wherein
the amino acid sequence of the heavy-chain CDR1 is the amino acid sequence represented by SEQ ID NO: 1,
the amino acid sequence of the heavy-chain CDR2 is the amino acid sequence represented by SEQ ID NO: 2,
the amino acid sequence of the heavy-chain CDR3 is the amino acid sequence represented by SEQ ID NO: 3,
the amino acid sequence of the light-chain CDR1 is the amino acid sequence represented by SEQ ID NO: 4,
the amino acid sequence of the light-chain CDR2 is the amino acid sequence represented by SEQ ID NO: 5,
the amino acid sequence of the light-chain CDR3 is the amino acid sequence represented by SEQ ID NO: 6,
the amino acid sequence of the heavy-chain FR1 is the amino acid sequence represented by SEQ ID NO: 17,
the amino acid sequence of the heavy-chain FR2 is the amino acid sequence represented by SEQ ID NO: 18,
the amino acid sequence of the heavy-chain FR3 is the amino acid sequence represented by SEQ ID NO: 19,
the amino acid sequence of the heavy-chain FR4 is the amino acid sequence represented by SEQ ID NO: 20,
the amino acid sequence of the light-chain FRI is the amino acid sequence represented by SEQ ID NO: 21,
the amino acid sequence of the light-chain FR2 is the amino acid sequence represented by SEQ ID NO: 22,
the amino acid sequence of the light-chain FR3 is the amino acid sequence represented by SEQ ID NO: 23, and
the amino acid sequence of the light-chain FR4 is the amino acid sequence represented by SEQ ID NO: 24,
to a human subject,
wherein said anti-podoplanin antibody and antigen-binding region thereof specifically bind to the PLAG4 domain of human podoplanin.

10. A pharmaceutical composition, comprising:
an effective amount for specifically binding to podoplanin of an isolated mouse-human chimeric anti-podoplanin antibody, or an antibody fragment thereof, comprising an antigen-binding region, which comprises variable regions comprising the following amino acid sequences,
the amino acid sequences of the heavy-chain FRs 1 to 4 and the light-chain FRs 1 to 4 optionally have a sequence identity of not less than 90% to the amino acid sequences represented by SEQ ID NO: 17 to 24 below, respectively,
wherein
the amino acid sequence of the heavy-chain CDR1 is the amino acid sequence represented by SEQ ID NO: 1,
the amino acid sequence of the heavy-chain CDR2 is the amino acid sequence represented by SEQ ID NO: 2,
the amino acid sequence of the heavy-chain CDR3 is the amino acid sequence represented by SEQ ID NO: 3,
the amino acid sequence of the light-chain CDR1 is the amino acid sequence represented by SEQ ID NO: 4,
the amino acid sequence of the light-chain CDR2 is the amino acid sequence represented by SEQ ID NO: 5,
the amino acid sequence of the light-chain CDR3 is the amino acid sequence represented by SEQ ID NO: 6,
the amino acid sequence of the heavy-chain FR1 is the amino acid sequence represented by SEQ ID NO: 17,
the amino acid sequence of the heavy-chain FR2 is the amino acid sequence represented by SEQ ID NO: 18,
the amino acid sequence of the heavy-chain FR3 is the amino acid sequence represented by SEQ ID NO: 19,
the amino acid sequence of the heavy-chain FR4 is the amino acid sequence represented by SEQ ID NO: 20,
the amino acid sequence of the light-chain FR1 is the amino acid sequence represented by SEQ ID NO: 21,
the amino acid sequence of the light-chain FR2 is the amino acid sequence represented by SEQ ID NO: 22,
the amino acid sequence of the light-chain FR3 is the amino acid sequence represented by SEQ ID NO: 23, and
the amino acid sequence of the light-chain FR4 is the amino acid sequence represented by SEQ ID NO: 24,
and a pharmaceutically acceptable carrier,
wherein said anti-podoplanin antibody and antigen-binding region thereof specifically bind to the PLAG4 domain of human podoplanin.

11. The pharmaceutical composition according to claim 10, wherein said isolated mouse-human chimeric anti-podoplanin antibody, or an antibody fragment thereof is present in a therapeutically effective amount effective to inhibit the binding between podoplanin and CLEC-2.

12. The pharmaceutical composition according to claim 11, wherein said isolated mouse-human chimeric anti-podoplanin antibody, or an antibody fragment thereof is present in a therapeutically effective amount effective to inhibit platelet aggregation.

* * * * *

SEQUENCE LISTING

<160> NUMBER OF SEQ ID NOS: 52

<210> SEQ ID NO 1
<211> LENGTH: 10
<212> TYPE: PRT
<213> ORGANISM: Mus musculus

```
<400> SEQUENCE: 1

Gly Phe Thr Phe Ser Gly Phe Gly Met Leu
1               5                   10

<210> SEQ ID NO 2
<211> LENGTH: 17
<212> TYPE: PRT
<213> ORGANISM: Mus musculus

<400> SEQUENCE: 2

Tyr Ile Ser Ser Val Ser Ser Arg Ile Tyr Tyr Ala Asp Thr Val Lys
1               5                   10                  15

Gly

<210> SEQ ID NO 3
<211> LENGTH: 10
<212> TYPE: PRT
<213> ORGANISM: Mus musculus

<400> SEQUENCE: 3

Glu Ser Tyr Gly Pro Ala Trp Phe Ala Tyr
1               5                   10

<210> SEQ ID NO 4
<211> LENGTH: 16
<212> TYPE: PRT
<213> ORGANISM: Mus musculus

<400> SEQUENCE: 4

Arg Ser Ser Gln His Ile Val His Ile Asp Gly Asn Thr Tyr Leu Glu
1               5                   10                  15

<210> SEQ ID NO 5
<211> LENGTH: 7
<212> TYPE: PRT
<213> ORGANISM: Mus musculus

<400> SEQUENCE: 5

Lys Val Ser Asn Arg Phe Ser
1               5

<210> SEQ ID NO 6
<211> LENGTH: 9
<212> TYPE: PRT
<213> ORGANISM: Mus musculus

<400> SEQUENCE: 6

Phe Gln Gly Ser His Val Pro Tyr Thr
1               5

<210> SEQ ID NO 7
<211> LENGTH: 25
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 8
<211> LENGTH: 14
```

```
<212> TYPE: PRT
<213> ORGANISM: Homo sapiens

<400> SEQUENCE: 8

Trp Val Arg Gln Ala Pro Gly Lys Gly Leu Glu Trp Val Ala
 1               5                  10

<210> SEQ ID NO 9
<211> LENGTH: 32
<212> TYPE: PRT
<213> ORGANISM: Homo sapiens

<400> SEQUENCE: 9

Arg Phe Thr Ile Ser Arg Asp Asn Ala Lys Asn Ser Leu Tyr Leu Gln
 1               5                  10                  15

Met Asn Ser Leu Arg Ala Glu Asp Thr Ala Val Tyr Tyr Cys Ala Arg
                20                  25                  30

<210> SEQ ID NO 10
<211> LENGTH: 11
<212> TYPE: PRT
<213> ORGANISM: Homo sapiens

<400> SEQUENCE: 10

Trp Gly Gln Gly Thr Leu Val Thr Val Ser Ser
 1               5                  10

<210> SEQ ID NO 11
<211> LENGTH: 23
<212> TYPE: PRT
<213> ORGANISM: Homo sapiens

<400> SEQUENCE: 11

Asp Ile Val Met Thr Gln Ser Pro Leu Ser Leu Pro Val Thr Pro Gly
 1               5                  10                  15

Glu Pro Ala Ser Ile Ser Cys
                20

<210> SEQ ID NO 12
<211> LENGTH: 15
<212> TYPE: PRT
<213> ORGANISM: Homo sapiens

<400> SEQUENCE: 12

Trp Tyr Leu Gln Lys Pro Gly Gln Ser Pro Gln Leu Leu Ile Tyr
 1               5                  10                  15

<210> SEQ ID NO 13
<211> LENGTH: 32
<212> TYPE: PRT
<213> ORGANISM: Homo sapiens

<400> SEQUENCE: 13

Gly Val Pro Asp Arg Phe Ser Gly Ser Gly Ser Gly Thr Asp Phe Thr
 1               5                  10                  15

Leu Lys Ile Ser Arg Val Glu Ala Glu Asp Val Gly Val Tyr Tyr Cys
                20                  25                  30

<210> SEQ ID NO 14
<211> LENGTH: 10
<212> TYPE: PRT
<213> ORGANISM: Homo sapiens

<400> SEQUENCE: 14
```

```
Phe Gly Gly Gly Thr Lys Val Glu Ile Lys
1               5                   10
```

<210> SEQ ID NO 15
<211> LENGTH: 14
<212> TYPE: PRT
<213> ORGANISM: Homo sapiens

<400> SEQUENCE: 15

```
Trp Val Arg Gln Ala Pro Gly Lys Gly Leu Glu Trp Val Ser
1               5                   10
```

<210> SEQ ID NO 16
<211> LENGTH: 32
<212> TYPE: PRT
<213> ORGANISM: Homo sapiens

<400> SEQUENCE: 16

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 17
<211> LENGTH: 25
<212> TYPE: PRT
<213> ORGANISM: Mus musculus

<400> SEQUENCE: 17

```
Asp Val Gln Leu Val Glu Ser Gly Gly Leu Val Gln Pro Gly Gly
1               5                   10                  15

Ser Arg Lys Leu Ser Cys Ala Ala Ser
            20                  25
```

<210> SEQ ID NO 18
<211> LENGTH: 14
<212> TYPE: PRT
<213> ORGANISM: Mus musculus

<400> SEQUENCE: 18

```
Trp Val Arg Gln Ala Pro Glu Lys Gly Leu Glu Trp Val Ala
1               5                   10
```

<210> SEQ ID NO 19
<211> LENGTH: 32
<212> TYPE: PRT
<213> ORGANISM: Mus musculus

<400> SEQUENCE: 19

```
Arg Phe Thr Ile Ser Arg Asp Asn Pro Lys Asn Thr Leu Phe Leu Gln
1               5                   10                  15

Met Thr Ser Leu Arg Ser Glu Asp Thr Ala Met Tyr Tyr Cys Ala Arg
            20                  25                  30
```

<210> SEQ ID NO 20
<211> LENGTH: 11
<212> TYPE: PRT
<213> ORGANISM: Mus musculus

<400> SEQUENCE: 20

```
Trp Gly Gln Gly Thr Leu Val Thr Val Ser Ala
1               5                   10
```

<210> SEQ ID NO 21
<211> LENGTH: 23
<212> TYPE: PRT
<213> ORGANISM: Mus musculus

<400> SEQUENCE: 21

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 22
<211> LENGTH: 15
<212> TYPE: PRT
<213> ORGANISM: Mus musculus

<400> SEQUENCE: 22

Trp Tyr Leu Gln Gln Pro Gly Gln Ser Pro Lys Leu Leu Ile Tyr
1               5                   10                  15

<210> SEQ ID NO 23
<211> LENGTH: 32
<212> TYPE: PRT
<213> ORGANISM: Mus musculus

<400> SEQUENCE: 23

Gly Val Pro Asp Arg Phe Ser Gly Ser Gly Ser Gly Thr Asp Phe Thr
1               5                   10                  15

Leu Arg Ile Ser Arg Val Glu Ala Glu Asp Leu Gly Val Tyr Tyr Cys
            20                  25                  30

<210> SEQ ID NO 24
<211> LENGTH: 10
<212> TYPE: PRT
<213> ORGANISM: Mus musculus

<400> SEQUENCE: 24

Phe Gly Gly Gly Thr Lys Leu Glu Met Lys
1               5                   10

<210> SEQ ID NO 25
<211> LENGTH: 327
<212> TYPE: PRT
<213> ORGANISM: Homo sapiens

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

```
Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 26
<211> LENGTH: 107
<212> TYPE: PRT
<213> ORGANISM: Homo sapiens

<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 27
<211> LENGTH: 30
<212> TYPE: DNA
<213> ORGANISM: Mus musculus

<400> SEQUENCE: 27
```
ggattcactt tcagtggctt tggaatgctc                                           30

<210> SEQ ID NO 28
<211> LENGTH: 51
<212> TYPE: DNA
<213> ORGANISM: Mus musculus

<400> SEQUENCE: 28
tacattagta gtgtcagtag tagaatctac tatgcagaca cagtgaaggg t                   51

<210> SEQ ID NO 29
<211> LENGTH: 30
<212> TYPE: DNA
<213> ORGANISM: Mus musculus

<400> SEQUENCE: 29
gaatcctacg gccccgcctg gtttgcttac                                           30

<210> SEQ ID NO 30
<211> LENGTH: 48
<212> TYPE: DNA
<213> ORGANISM: Mus musculus

<400> SEQUENCE: 30
agatctagtc agcacattgt acatattgat ggaaacacct atttagaa                       48

<210> SEQ ID NO 31
<211> LENGTH: 21
<212> TYPE: DNA
<213> ORGANISM: Mus musculus

<400> SEQUENCE: 31
aaagtttcca accgattttc t                                                    21

<210> SEQ ID NO 32
<211> LENGTH: 27
<212> TYPE: DNA
<213> ORGANISM: Mus musculus

<400> SEQUENCE: 32
tttcaaggtt cacatgttcc gtacacg                                              27

<210> SEQ ID NO 33
<211> LENGTH: 75
<212> TYPE: DNA
<213> ORGANISM: Homo sapiens

<400> SEQUENCE: 33
gaggtgcagc tggtggagtc tgggggaggc ttggtccagc ctggggggtc cctgagactc          60
tcctgtgcag cctct                                                           75

<210> SEQ ID NO 34
<211> LENGTH: 42
<212> TYPE: DNA
<213> ORGANISM: Homo sapiens

<400> SEQUENCE: 34
tgggtccgcc aggctccagg gaaggggctg gagtgggtgg cc                             42

<210> SEQ ID NO 35
<211> LENGTH: 96
<212> TYPE: DNA
<213> ORGANISM: Homo sapiens

<400> SEQUENCE: 35
cgattcacca tctccagaga caacgccaag aactcactgt atctgcaaat gaacagcctg    60
agagccgagg acacggctgt gtattactgt gcgaga    96

<210> SEQ ID NO 36
<211> LENGTH: 33
<212> TYPE: DNA
<213> ORGANISM: Homo sapiens

<400> SEQUENCE: 36
tggggccagg gcaccctggt caccgtctcc tca    33

<210> SEQ ID NO 37
<211> LENGTH: 69
<212> TYPE: DNA
<213> ORGANISM: Homo sapiens

<400> SEQUENCE: 37
gatattgtga tgactcagtc tccactctcc ctgcccgtca cccctggaga gccggcctcc    60
atctcctgc    69

<210> SEQ ID NO 38
<211> LENGTH: 45
<212> TYPE: DNA
<213> ORGANISM: Homo sapiens

<400> SEQUENCE: 38
tggtacctgc agaagccagg gcagtctcca cagctcctga tctat    45

<210> SEQ ID NO 39
<211> LENGTH: 96
<212> TYPE: DNA
<213> ORGANISM: Homo sapiens

<400> SEQUENCE: 39
ggagtcccag acaggttcag tggcagtggg tcaggcactg atttcacact gaaaatcagc    60
agggtggagg ctgaggatgt tggagtttat tactgc    96

<210> SEQ ID NO 40
<211> LENGTH: 30
<212> TYPE: DNA
<213> ORGANISM: Homo sapiens

<400> SEQUENCE: 40
ttcggcggag ggaccaaggt ggagatcaaa    30

<210> SEQ ID NO 41
<211> LENGTH: 42
<212> TYPE: DNA
<213> ORGANISM: Homo sapiens

<400> SEQUENCE: 41
tgggtccgcc aggctccagg gaaggggctg gagtgggtct ca    42

<210> SEQ ID NO 42
<211> LENGTH: 96
<212> TYPE: DNA
<213> ORGANISM: Homo sapiens

<400> SEQUENCE: 42
agattcacca tctccagaga caattccaag aacacgctgt atcttcaaat gaacagcctg    60
agagccgagg acacggctgt gtattactgt gcgaga                              96

<210> SEQ ID NO 43
<211> LENGTH: 981
<212> TYPE: DNA
<213> ORGANISM: Homo sapiens

<400> SEQUENCE: 43
gcttccacca agggaccatc cgtcttcccc ctggcgccct gctccaggag cacctccgag    60
agcacagccg ccctgggctg cctggtcaag gactacttcc ccgaaccggt gacggtgtcg   120
tggaactcag gcgccctgac cagcggcgtg cacaccttcc cggctgtcct acagtcctcc   180
ggactctact ccctcagcag cgtggtgacc gtgccctcca gcagcttggg cacgaagacc   240
tacacctgca acgtagatca caagcccagc aacaccaagg tggacaagag agttgagtcc   300
aaatatggtc ccccatgccc accatgccca gcacctgagt tcctgggggg accatcagtc   360
ttcctgttcc cccaaaaacc caaggacact ctcatgatct cccggacccc tgaggtcacg   420
tgcgtggtgg tggacgtgag ccaggaagac cccgaggtcc agttcaactg gtacgtggat   480
ggcgtggagg tgcataatgc caagacaaag ccgcgggagg agcagttcaa cagcacgtac   540
cgtgtggtca gcgtcctcac cgtcctgcac caggactggc tgaacggcaa ggagtacaag   600
tgcaaggtct ccaacaaagg cctcccgtcc tccatcgaga aaaccatctc caaagccaaa   660
gggcagcccc gagagccaca ggtgtacacc ctgcccccat cccaggagga tgaccaag    720 aaccaggtca gcctgacctg cctggtcaaa ggcttctacc ccagcgacat cgccgtggag   780
tgggagagca atgggcagcc ggagaacaac tacaagacca cgcctcccgt gctggactcc   840
gacggctcct tcttcctcta cagcaggcta accgtggaca gagcaggtg gcaggagggg    900 aatgtcttct catgctccgt gatgcatgag gctctgcaca accactacac acagaagagc   960
ctctccctgt ctctgggtaa a                                             981

<210> SEQ ID NO 44
<211> LENGTH: 321
<212> TYPE: DNA
<213> ORGANISM: Homo sapiens

<400> SEQUENCE: 44
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321

<210> SEQ ID NO 45
<211> LENGTH: 75
<212> TYPE: DNA
<213> ORGANISM: Mus musculus

<400> SEQUENCE: 45
gatgtgcaac tggtggagtc tggggaggc ttggtgcagc ctggagggtc ccggaaactc     60
tcctgtgcag cctct                                                    75

```
<210> SEQ ID NO 46
<211> LENGTH: 42
<212> TYPE: DNA
<213> ORGANISM: Mus musculus

<400> SEQUENCE: 46
tgggttcgtc aggctccaga gaagggctg gagtgggtcg ca                          42

<210> SEQ ID NO 47
<211> LENGTH: 96
<212> TYPE: DNA
<213> ORGANISM: Mus musculus

<400> SEQUENCE: 47
cgattcacca tctccagaga caatcccaag aacaccctgt tcctgcaaat gaccagtctg      60
aggtctgagg acacggccat gtattactgt gcaaga                               96

<210> SEQ ID NO 48
<211> LENGTH: 33
<212> TYPE: DNA
<213> ORGANISM: Mus musculus

<400> SEQUENCE: 48
tggggccaag ggactctggt cactgtctct gca                                  33

<210> SEQ ID NO 49
<211> LENGTH: 69
<212> TYPE: DNA
<213> ORGANISM: Mus musculus

<400> SEQUENCE: 49
gatgtcttga tgacccaaac tccactctcc ctgccggtca gtcttggaga tcaagcctcc      60
atctcttgc                                                             69

<210> SEQ ID NO 50
<211> LENGTH: 45
<212> TYPE: DNA
<213> ORGANISM: Mus musculus

<400> SEQUENCE: 50
tggtacctgc agcaaccagg ccagtctcca aagctcctga tctac                     45

<210> SEQ ID NO 51
<211> LENGTH: 96
<212> TYPE: DNA
<213> ORGANISM: Mus musculus

<400> SEQUENCE: 51
ggggtcccag acaggttcag tggcagtgga tcagggacag atttcacact caggatcagc     60
agagtggagg ctgaggatct gggagtttat tactgc                               96

<210> SEQ ID NO 52
<211> LENGTH: 30
<212> TYPE: DNA
<213> ORGANISM: Mus musculus

<400> SEQUENCE: 52
ttcggagggg ggaccaagct ggaaatgaaa                                      30
```